(12) United States Patent
Ramsey, III

(10) Patent No.: US 10,918,838 B2
(45) Date of Patent: Feb. 16, 2021

(54) DEVICE FOR CONTROLLING BLEEDING FROM A BALLISTIC PENETRATING OR PERFORATING WOUND

(71) Applicant: Maynard Ramsey, III, Tampa, FL (US)

(72) Inventor: Maynard Ramsey, III, Tampa, FL (US)

( * ) Notice: Subject to any disclaimer, the term of this patent is extended or adjusted under 35 U.S.C. 154(b) by 268 days.

(21) Appl. No.: 14/017,272

(22) Filed: Sep. 3, 2013

(65) Prior Publication Data

US 2014/0142504 A1 May 22, 2014

Related U.S. Application Data

(63) Continuation of application No. 10/917,019, filed on Aug. 11, 2004, now abandoned.

(60) Provisional application No. 60/496,051, filed on Aug. 17, 2003.

(51) Int. Cl.
| | | |
|---|---|---|
| *A61M 25/10* | (2013.01) | |
| *A61M 25/01* | (2006.01) | |
| *A61B 17/12* | (2006.01) | |
| *A61L 29/16* | (2006.01) | |
| *A61M 25/06* | (2006.01) | |

(52) U.S. Cl.
CPC ....... *A61M 25/10* (2013.01); *A61B 17/12136* (2013.01); *A61L 29/16* (2013.01); *A61M 25/0102* (2013.01); *A61M 2025/0681* (2013.01); *A61M 2025/1081* (2013.01)

(58) Field of Classification Search
CPC ............ A61B 17/12022; A61B 17/132; A61B 17/12136; A61M 25/10; A61M 25/102; A61M 2025/0681; A61M 2025/105; A61M 2025/1081; A61M 2025/1086; A61M 2025/10183
See application file for complete search history.

(56) References Cited

U.S. PATENT DOCUMENTS

| | | | | |
|---|---|---|---|---|
| 4,832,691 A | * | 5/1989 | Witzel | A61M 25/10183 604/98.02 |
| 5,213,576 A | * | 5/1993 | Abiuso | A61M 25/104 604/101.02 |
| 5,246,421 A | * | 9/1993 | Saab | A61M 25/104 128/898 |
| 5,345,937 A | * | 9/1994 | Middleman et al. | A61B 1/00 600/434 |

(Continued)

*Primary Examiner* — Sarah W Aleman
(74) *Attorney, Agent, or Firm* — Frijouf, Rust & Pyle, P.A.

(57) ABSTRACT

A tamponade catheter is disclosed for controlling bleeding from a penetrating or perforating wound in a patient comprising a catheter having an inner catheter lumen with a non-elastic inflatable balloon secured to the catheter in fluid communication with an inner catheter lumen of the catheter. A removable outer sheath overlays the inflatable balloon for inserting the inflatable balloon within the wound of the patient. A bendable flexible stiffening stylet is receivable within the inner catheter lumen of the catheter to aid in navigating the catheter into the wound of the patient. The removable outer sheath and the stylet are removable for inflating the inflatable balloon by an introduction of a fluid through the inner catheter lumen of the catheter for enabling the inflated non-elastic inflatable balloon to create pressure within the wound of the patient to control bleeding therefrom.

18 Claims, 10 Drawing Sheets

(56) References Cited

U.S. PATENT DOCUMENTS

| | | | | |
|---|---|---|---|---|
| 5,540,711 A * | 7/1996 | Kieturakis | ......... | A61B 17/0218 |
| | | | | 600/204 |
| 5,571,089 A * | 11/1996 | Crocker | ............. | A61M 25/1011 |
| | | | | 604/103.01 |
| 5,571,181 A * | 11/1996 | Li | ...................... | A61B 17/0057 |
| | | | | 128/DIG. 8 |
| 5,653,726 A * | 8/1997 | Kieturakis | ......... | A61B 17/0218 |
| | | | | 128/898 |
| 5,868,707 A * | 2/1999 | Williams | .............. | A61M 25/10 |
| | | | | 604/103 |
| 6,306,154 B1 * | 10/2001 | Hudson | .............. | A61B 17/0057 |
| | | | | 606/196 |
| 6,592,602 B1 * | 7/2003 | Peartree | ........... | A61B 17/00234 |
| | | | | 600/204 |
| 6,733,473 B1 * | 5/2004 | Reifart | ................ | A61M 25/104 |
| | | | | 604/96.01 |
| 2002/0077656 A1 * | 6/2002 | Ginn | .................. | A61B 17/0057 |
| | | | | 606/213 |

* cited by examiner

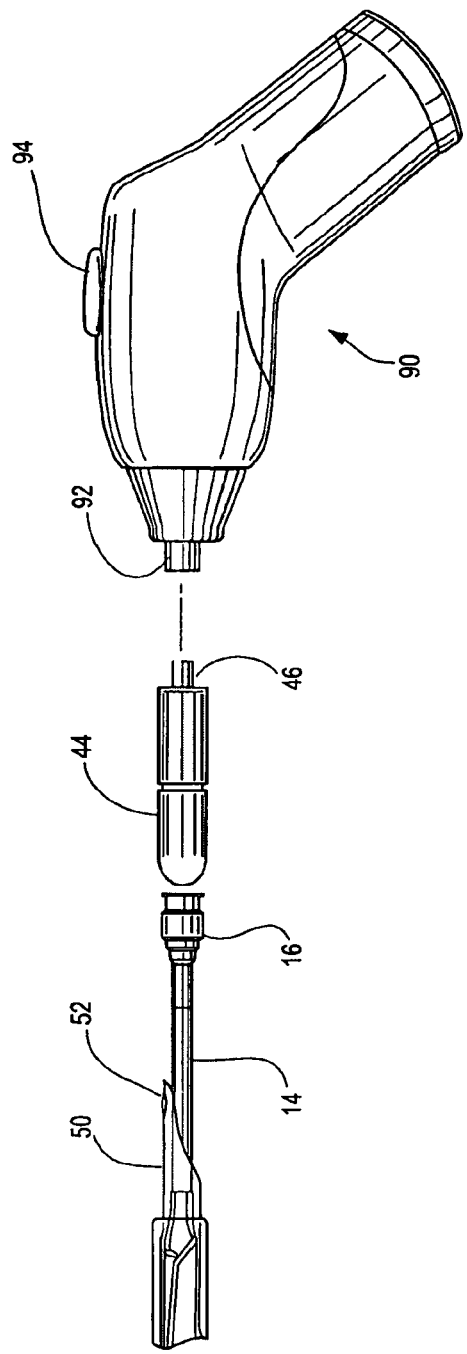

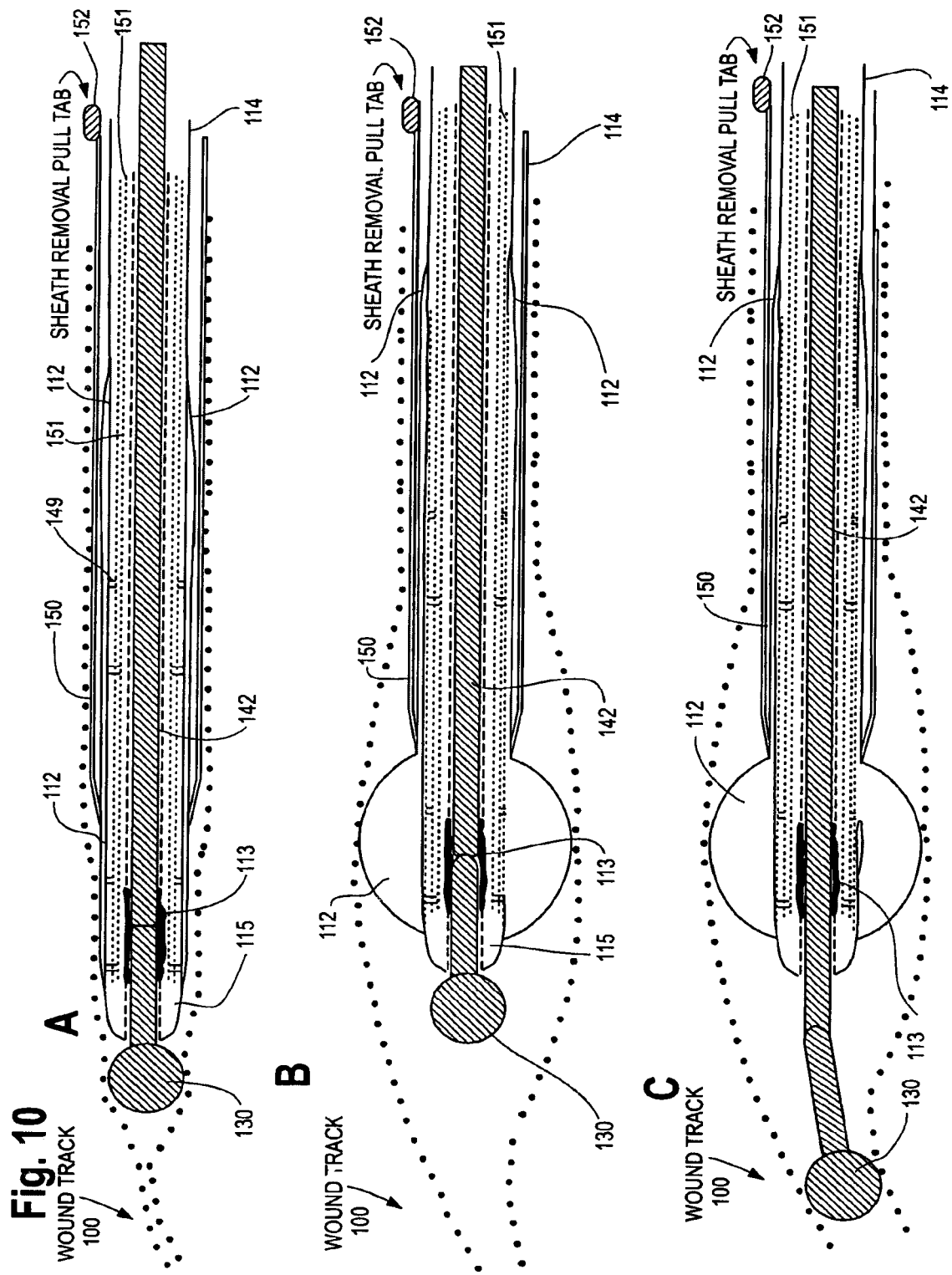

DEVICE FOR CONTROLLING BLEEDING FROM A BALLISTIC PENETRATING OR PERFORATING WOUND

CROSS-REFERENCE TO RELATED APPLICATIONS

This Application is a continuation of U.S. application Ser. No. 10/917,019 filed Aug. 11, 2004, U.S. application Ser. No. 10/917,019 filed Aug. 11, 2004 claims benefit of U.S. Patent Provisional application No. 60/496,051 filed Aug. 17, 2003, All subject matter set forth in application Ser. No. 10/917,019 filed Aug. 11, 2004 and application No. 60/496,051 filed Aug. 17, 2003 is hereby incorporated by reference into the present application as if fully set forth herein.

FEDERALLY SPONSORED RESEARCH

Not Applicable

SEQUENCE LISTING OR PROGRAM

Not Applicable

FIELD OF INVENTION

The present invention relates generally to devices and methods for controlling major hemorrhage in living creatures. More specifically, it relates to an internal compression tamponade catheter system, generally in a catheter form, but optionally in a bag or bladder form, which incorporates design elements specifically to tamponade such hemorrhage but equally importantly, it contains elements that are specifically designed to aid its insertion deep into tissue spaces from which blood loss is occurring. Generally such tissue spaces are wound tracks caused by penetrating injuries that cause major and often fatal hemorrhage, but such tissue spaces in which my catheter system is applicable also includes body cavities in which one or more organs have been damaged by blunt or penetrating trauma ad also by surgical exploration or iatrogenic surgical wounds. My system, and its method of use for slowing or stopping bleeding, represents a new system with multiple substantial improvements over prior art devices for controlling hemorrhage. Such improvements over prior art include, without limitation: a catheter shaft which optionally has at least one of lumens to house a stylet, inflate the balloon, dispense clot enhancing substances in to the wound, drain blood and other fluids from the tissue space, the expandable portion of my device, commonly called the balloon, is much improved over prior art in its size, its shape, its large potential volume and its construction of puncture resistant material, and it is a balloon design which thus permits the accurate measurement of the pressure exerted on the wound track by measuring the pressure within the nonelastic balloon. An equally important aspect of my catheter system is that provides an equally important introduction system for guiding it into tortuous wound tracks such that it is safely and easily deployed deep into the tissue track to be compressed in order to stop bleeding or prevent future bleeding within or adjacent the wound track. The hemostatic effect is due to compression of the bleeding tissues within the range of the pressure field generated by the expansible device placed within the tissue, and optionally, by clotting induced by clot promoting agents applied to the surface of the catheter or the expansible portion of the device before insertion into the wound, or such clot promoting agents can be administered through small openings in the catheter and optionally, through small pressure sensitive openings in the expansible portion of the catheter.

The expansible form is most generally a light weight bladder, cylindrical or ovoid in shape, designed to be filled with a liquid or a gas in order cause it to expand and hence to generate the pressure field applied to the bleeding tissue to cause tamponade of that bleeding. It is often referred to as a "balloon" in this patent application for simplicity of communication, but it is to be understood, my inventive tamponadding expansile device is not a balloon in the child's toy sense of the word. It is tough and constructed of nonelastic material that is also puncture resistant.

BACKGROUND OF THE INVENTION

Discussion of Prior Art

It can be appreciated that bleeding is a major cause of morbidity and mortality in persons and animals who have injuries, surgeries, or disease processes that result in severe bleeding. This severe bleeding can be due to disruption of tissue due to blunt or penetrating trauma or to surgical and-or disease processes within the body. That is, when a person has a disease process which causes disruption of blood vessels, such as aneurysms which spontaneously rupture, bleeding can occur without the external application of any injurious force or agent. In other cases, trauma is the cause of significant bleeding and such trauma can be due to blunt injury such as that often sustained in a motor vehicle accident or from falling from a height, or due to penetrating trauma such as that inflicted by a knife or a ballistic missile such as from shrapnel or a bullet. Penetrating trauma is further classified as penetrating or perforating (or thru-and-thru). Penetrating wounds are where penetrating injuries have an entry wound through the skin surface, but do not produce an exit skin wound since the depth of penetration of the missile or sharp object is not sufficient to pass completely through the portion of the body that is injured. A missile or knife wound which both enters and exits the body is termed a perforating (or thru-and-thru) wound. Both types of penetrating trauma wounds can cause substantial and often fatal bleeding. Where such injuries produce substantial bleeding as from a major artery or vein, or from the liver or spleen, rapid control of such bleeding or hemorrhage is crucial if the injured person is to survive. It is estimated that 50% of military persons killed in action (KIA) die of hemorrhage and of those 50% that die of hemorrhage, most will die within one hour of wounding, even though approximately 20-25% have correctable injuries if they could only be kept alive long enough to be transported to a site of definitive care, typically an operating room (OR). Further, analysis of civilian victims of penetrating trauma due to gunshot and stab wounds, not involving the head and arriving alive for treatment at a major metropolitan trauma center, shows that approximately 12% die of exsanguination due to their wounds even after they reach the hospital alive. Many more die of exsanguination before arrival at the hospital.

The methods of controlling such major, and often fatal, hemorrhage have changed little over the last 2000 years when battle injuries were treated, as now, with direct external compression of the wound to stop bleeding, and if unsuccessful, treated with a limb encircling external tourniquet applied proximal to the bleeding wound of an extremity. The simplest of these two methods is to apply direct compression to the bleeding wound using the hand or the hand covered with cloth or gauze. Such force applied to the wound will often, at least temporarily, stop the bleeding by compressing the bleeding vessels sufficiently that the internal circulatory pressure in both veins and arteries is overcome by the external compression force and hence bleeding is prevented by this external pressure which is greater than the internal pressure within the veins and arteries, such internal pressure is referred to as the arterial blood pressure and the venous pressure. However, this externally applied pressure must be greater than the blood pressure if arterial bleeding is the cause of the major hemorrhage, and it must be maintained for a prolonged period of time, often until the victim reaches definitive care, otherwise the bleeding will start again when the external pressure is removed. If the wound is on an extremity, the compressing cloth or bandage can be tied snugly, but unfortunately, this snug tying often becomes like a loose tourniquet and can actually increase bleeding from veins if sufficient direct pressure is not applied directly to the bleeding wound.

To enhance this direct compression method of hemorrhage control, coagulation enhancing substances such as human or bovine fibrin, chitosan, various granular and powdered form compounds, as well as freeze dried platelets have been applied to external bandages or to the wound directly to encourage clotting of the underlying blood vessels and hence stop significant bleeding. Unfortunately, for these clot promoters to be effective, the wound must be such that the promoters can come into direct contact with the bleeding vessels in order to be effective and hence such enhanced direct compression bandages containing clot promoters, or the direct pressure on a wound into which a clot promoter has been poured, are not more effective than their un-enhanced counterpart stopping bleeding from wounds in which the bleeding vessels are deep within the wound and thus not reachable by traditional methods to achieve the required direct contact by the clot promoters. Additionally, direct pressure is of no use, with or without clot promoters, for stanching bleeding from wounds which are deep within a body cavity such as the shoulder and axilla, pelvis, abdomen, or thorax or any wounds beneath or protected by bone which prevents the direct compressive pressure from reaching the injured vessels.

If the wound is on an extremity (arm or leg), an alternative method of stanching bleeding is the use of an external encircling tourniquet. An external encircling tourniquet is formed by any one of several methods, generally being constructed of cloth, leather, fabric webbing, or inflatable pneumatic cuff integral with the bandage. The tourniquet, regardless of construction, is tightened around the limb to stop bleeding by compressing all veins and arteries within the encircled limb. Some such tourniquets, generally of the pneumatic inflatable type, are used during surgical operations on limbs and are generally in the form of an inflatable pneumatic cuff, similar to a blood pressure cuff, that can be inflated with air to compress the limb to stop or prevent bleeding during surgery and provide a bloodless operative field. Such pneumatic tourniquets can also be used to stop bleeding due to trauma to an extremity. Regardless of the specific design of such external encircling tourniquets, the essential requirement for their proper function is that the tourniquet be so tightly constricted around the limb proximal to the bleeding wound that all of the arteries and the veins within the limb are totally occluded by the external pressure and consequently prevent blood from reaching the wound and being lost due to bleeding from the injured tissue. When properly applied to stop major bleeding due to injury to an extremity, arm or leg, the tourniquet is effective at preventing additional blood loss. If not applied tightly enough however, such a tourniquet can actually increase bleeding since it compresses the veins preventing any return of blood to the body from the limb, but insufficiently compresses the artery and hence additional blood enters the limb and is lost from the wound or extravasated into the wounded tissue itself. However, since all blood vessels are occluded by the tourniquet when properly applied, the limb tissue distal to the tourniquet (often such tissue is healthy and uninjured) is also rendered totally ischemic since all the distal tissue is without blood supply. Typically such limb ischemia can be tolerated for only 3-4 hours before the tissue distal to the tourniquet is killed and becomes necrotic from lack of blood supply, but severe injury has been caused by even less time of occlusion For example, if the injury producing significant bleeding is at the level of the mid-thigh and the tourniquet is applied at the level of the upper thigh above the injury, the bleeding will stop from the wound, but the entire leg will be rendered ischemic. Consequently, if the tourniquet is not removed within 3-6 hours, the entire limb will be dead and require amputation. Additionally, since the ischemic part of the limb distal to the tourniquet is slowly dying and releasing myoglobin from the ischemic muscle tissue, if the tourniquet is released after a period of 3-6 hrs, the patient may eventually die due to renal failure caused by the systemic circulation of the myoglobin which is toxic to the kidneys and which is released by the ischemic muscle into the blood stream after the tourniquet is released. Thus, in these circumstances, amputation of the limb, without release of the tourniquet, is the required treatment. Tourniquets may be lifesaving, but they can result in loss of limb and possibly life if used inappropriately.

Attempts have been made to use balloon type catheters to control hemorrhage within various organs and body cavities and many reports of these types of cases are reported in the medical literature. For example, there are reports of using a balloon tipped urinary bladder type catheter, commonly known as a Foley catheter, to tamponade bleeding from various superficial arteries such as the common carotid and for deeper vessels such as the subclavian artery and vein. This technique was reported by Gilroy, et al (*Injury* 23, (8) 557-559, 1992) using the Foley urinary catheter. Their attempts to tamponade penetrating stab wounds (SWs) and gunshot wounds (GSWs) with the Foley urinary catheter, with its very small balloon size of 15-20 ml, its suboptimal round balloon shape, and its difficulty of placement into the wound track, demonstrated somewhat disappointing overall results in that only 5 of 8 cases were successfully tamponadded. However, these were attempts made in the Emergency Department (ED) and not at surgery under anesthesia where more accurate placement might have been possible. However, the bleeding was successfully tamponadded in several cases and resulted in buying time for definitive treatment with ultimate survival and in some may have proven truly lifesaving.

The use of balloon tamponade for hemorrhage control has also been done during surgery. A report by Gonzalez, et al, (J Trauma 1997 August; 43(2):338-341) demonstrated eleven successful cases where a Foley catheter was used during surgery. The device was inserted through an intentionally made stab wound and manually positioned in the area of bleeding and left in place postoperatively for control of hemorrhage associated with penetrating wounds to the rectum and pre-sacrum vascular plexus.

Feliciano, et al (Amer J Surg 1990 December; 160:583-587) utilized a Fogarty vascular balloon embolectomy catheter during surgery in 12 patients to control hemorrhage from various head and neck wounds with generally favorable results. Other devices, specifically designed for tamponade of traumatically or surgically induced bleeding are the Cook "Liver Tamponade Balloon" and the Cook "Kaye Nephrostomy Catheter".

The "Liver Tamponade Balloon" utilizes a 16 French gauge catheter with an inflatable balloon and is suggested for tamponade of bleeding from penetrating trauma of the liver that cannot be controlled by liver packing. The balloon on this catheter is essentially a distensible, compliant (ie, elastic) silicon rubber balloon approximately 8 inches long is mounted (lies flush on the catheter shaft when uninflated) on the 16 Fr catheter. The catheter is inserted into the liver wound and inflated with 60 ml saline to apply internal pressure to the liver to tamponade bleeding. The device has an elastic silicon balloon which is designed to be inflated with a maximum of 60 ml of saline, but it must be inserted into the wound without an introduction system designed to assist such wound track introduction in the liver. That is, it has no introducer or mechanism to assist its insertion into the liver wound, relying on its own stiffness and user creativity to introduce it sufficiently deep to tamponade the bleeding. Also, since the balloon on the Liver Tamponade Balloon is elastic and requires internal pressure to inflate it, there is no method of knowing what actual pressure is being applied to the tissue by the balloon since the inflation of the balloon requires pressure. Thus, if someone inadvertently injected more than 60 ml of saline, the pressure in the wound track applied directly to the liver would increase and potentially split or fracture the delicate liver tissue resulting in greater injury. The same undesirable outcome might occur if the 60 ml of saline were injected into the balloon and the wound track in which the balloon was positioned was of insufficient size to accommodate even as little as the 60 ml without liver damage. The difficulty with this elastic balloon tamponade catheter design, and all such designs, is that since it takes positive pressure to distend the balloon even when it is unconstrained by tissue in a wound track, it is impossible to know how much of the distending pressure generated by the injection of the 60 ml of saline is contributing to distention of the balloon and how much is actually being applied to the wound track within the balloon. Too little wound track pressure may result in inadequate tamponade and too much wound track pressure may result in making the injury worse since it may split delicate or friable tissue.

Similarly, the Kaye Nephrostomy catheter is a small volume balloon catheter designed specifically for operative use in percutaneous nephrolithotomy procedures where bleeding from the kidney is excessive postoperatively. It includes a flexible stylet to stiffen the catheter to aid insertion into the surgically created, very small cavity in the kidney tissue. It is not designed for emergency treatment of penetrating traumatic wounds and its size and shape would make it unsuitable in general for treating traumatic penetrating trauma wounds.

In view of the foregoing description of the disadvantages inherent in the known types of devices and methods for stanching bleeding from wounds, several objects and advantages of the present patent application of Maynard Ramsey III for "INTERNAL COMPRESSION TOURNIQUET CATHETER SYSTEM AND METHOD FOR CONTROLLING HEMORRHAGE" are:

(a) to provide a highly reliable method for tamponadding internal hemorrhage due to penetrating trauma from shrapnel, gunshot, and stab wounds in both military and civilian environments;

(b) to provide a tamponade catheter system that is more effective than the existing devices used for tamponadding hemorrhage, such current devices being too small to tamponade large wound tracks, having no effective method to determine the tamponade force applied to the wounded tissue, since the balloon is elastic and distensible, and further these existing devices have no effective means for introducing and directing the tamponade catheter into deep internal penetrating wound tracks;

(d) to provide a tamponade catheter system which is inflated to tamponade bleeding using a known and measurable desired pressure which is therefore more gentle to tissues and more effective at controlling hemorrhage than the existing devices which suggest that a fixed volume of fluid be used to inflate the compression balloon;

(e) to provide a tamponade catheter system which utilizes a large volume inflatable balloon that requires essentially no pressure to be inflated to its maximum extent, and which is capable of safely being inflated with a gas, a liquid, or both, as compared to existing devices which require substantial pressure just to enlarge them slightly, and hence must for safety reasons be inflated with a sterile liquid in case of balloon rupture;

(f) to provide a tamponade catheter system which has a nonelastic balloon which is very of very large potential volume, which requires essentially zero pressure to inflate to its maximum when unconstrained, is flexible, and is conformable and hence can expand differentially to varying diameters and shapes along its length when inflated in wound tracks of variable shape, this being in contrast to the prior art devices which are constrained by their construction to maintain essentially a small spherical shape or a cylindrical shape with near constant diameter along its length;

(g) to provide a tamponade catheter system which utilizes an inflatable internal compression means, such as a noncompliant balloon, which is of large potential volume and which is flexible and hence more effective at controlling hemorrhage than the existing devices which are limited in volume to 60 ml or less and further, such prior art compression balloons are elastic in nature requiring a positive pressure to inflate them to their standard volume, thus preventing knowledge of how much pressure is actually being applied to the wound track by the compression balloon;

(h) to provide a tamponade catheter system which utilizes an inflatable internal compression means, such as a balloon, which is of long length, up to 46 cm, and large diameter, up to 16 cm in diameter when inflated with gas or liquid and hence is more effective at controlling hemorrhage from large or irregularly shaped wounds than the existing devices which are limited in length to 20 cm or less and limited in expanded diameter to 2.8 cm in diameter.

(i) to provide a tamponade catheter system which utilizes an inflatable internal compression means, such as a balloon, which is flat when uninflated, and of large width, up to 25 cm in wide when not inflated, and of long length, up to 46 cm, and hence effective at controlling hemorrhage from fractured organs such as the liver or spleen when used as a variable pressure packing device for applying even and adjustable pressure to control traumatic and/or surgically caused hemorrhage, such inflatable hemorrhage controlling packing devices being unknown in the prior art in which liver packing is done with gauze sponges which do not permit pressure adjustment once placed and the wound closed, which are a good culture medium for bacterial growth, and which require the patient to be returned to surgery for their ultimate removal;

(j) to provide a tamponade catheter system which comprises a catheter, with a tamponade balloon made of gas impervious coated fabric material, or other such penetration resistant material, such that during placement within the wound track and when the balloon is pressurized to tamponade bleeding, the balloon will not be punctured by sharp fragments of bone or shrapnel;

(k) to provide a tamponade catheter which in yet another embodiment comprises a catheter with a tamponade balloon made of two layers of material, one being a tough outer fabric of penetration resistant material layer, either coated fabric or straight polymer, and an inner polymer material layer such that a puncture in the outer material will not result in a puncture of the inner material and hence prevent the loss of pressure which would result if both layers were pierced by a sharp object in contact with the tamponadding balloon member;

(l) to provide a tamponade catheter which optionally utilizes one or more outer protective sheath(s) over the inflatable internal compression balloon means when said balloon is deflated, wrapped or folded snuggly around the catheter shaft and ready for insertion into the wound track such that during placement within the wound track, the balloon, regardless of its construction, is thus protected by the sheath(s) and hence is not subject to damage from missile or bone fragments during insertion as would occur with existing devices which do not utilize such a protective sheath, or puncture resistant balloon material:

(m) to provide a tamponade catheter which optionally utilizes a protective sheath over the inflatable internal compression balloon means, such that said sheath can be partially retracted towards the proximal end of the catheter and the balloon in order to expose a portion of the distal balloon to allow expansion of only that distal portion of the balloon upon inflation of the balloon for bleeding tamponade, where the portion of the protective sheath left in place over the balloon proximally assuring that portion of the balloon is not subject to damage from missile or bone fragments as it is with existing devices which have no protective sheath;

(n) to provide a tamponade catheter which optionally utilizes a protective sheath over the inflatable internal compression balloon means, such that said sheath can be partially retracted to expose a short segment of the balloon distally such that when said short distal segment of the balloon is inflated, the small exposed and inflated portion of the distal portion of the balloon forms a "pilot balloon" to provide expansion of the wound track as an aid to further catheter insertion into the wound track, such pilot balloon inflation and deflation means and method for wound track navigation facilitation not being available in prior art devices;

(o) to provide a tamponade catheter which optionally utilizes a flexible, but bendable internal stylet fully contained within a catheter lumen and extending to the distal tip of the catheter, and where the stylet can be bent at the tip to facilitate wound track navigation of the tamponade catheter into curved or irregular shaped wound tracks, such bendable stylets not being available in current tamponade devices;

(p) to provide a tamponade catheter which optionally utilizes a bendable stylet fully contained with in the catheter and extending to the tip of the tamponade catheter and which can be rotated by an external stylet handle on said stylet proximal end of the stylet, said stylet handle being constructed so that it is easy to grasp and so that the user knows by tactile feel, or by the sight of the stylet handle, in which direction the bend or curve in the distal catheter tip is pointing even when the tip of the catheter and the stylet are obscured from view, being within the wound track, said orientation sensing further facilitating wound track navigation of my tamponade catheter system, such malleable and oriented by feel stylets not being available in prior art devices;

(q) to provide a tamponade catheter which optionally utilizes a catheter tip construction the wound track exploring tip of bulbous or enlarged rounded dimensions, to prevent snagging or hanging-up of the catheter tip during insertion into the wound and during its full navigation of the wound track, such bulbous or enlarged rounded tipped catheters not being available in current devices which renders them difficult to insert into wound tracks;

(r) to provide a tamponade catheter system in another embodiment, which utilizes a bulbous or enlarged rounded tipped malleable stylet to prevent snagging in the wound track during insertion, and which has an external orientable stylet handle for rotating and pushing forward the stylet into the wound track, said stylet being constructed of a length of suitable material that is longer by several inches than the catheter shaft in which said stylet is contained, this construction of stylet and catheter are such that the stylet with its attached exploring tip protrudes through the distal end of the catheter shaft when advanced by pushing on the proximal stylet handle, where this bulbous tipped stylet can be inserted into the wound track ahead of the catheter for a few inches at a time such that the catheter can then pushed into the wound track over the previously advanced stylet, thus allowing incremental advancement of the catheter into difficult wound tracks before inflation of the tamponade balloon, such stylets and methods of wound track navigation not being available in current devices;

(s) to provide a tamponade catheter which utilizes a bulbous or enlarged rounded exploring tip attached to the distal tip of the catheter shaft where said exploring tip is comprised of an inner smaller diameter exploring tip, and removably positioned over it, a larger diameter outer exploring tip such that if the wound track is very small or pierces through bone which will not admit the larger diameter outer exploring tip, the larger outer exploring tip can be removed to allow wound track navigation using only the smaller inner exploring tip, such tips, whether multi sized or not are not available in prior art catheters;

(t) to provide a tamponade catheter system which utilizes a bulbous or rounded exploring tip attached to the catheter and where said exploring tip is comprised of an inner smaller diameter exploring tip attached to the distal end of the catheter, and the larger outer exploring tip is attached to the inner, smaller, exploring tip in a means that allows secure attachment but which permits manual removal without tools of the larger outer exploring tip should it be necessary due to a wound track of small dimensions.

(u) to provide a tamponade catheter system which utilizes a bulbous or rounded exploring tip and further comprising a puncture resistant balloon, an inner protective sheath for the balloon, and an outer stiffer introducer sheath into which the inner sheath and catheter-balloon assembly fits movably, but snuggly, such outer sheath both protecting the inner assembly and also providing additional stiffness to aid in finding and navigating the catheter assembly into the full length of the wound track, such outer stiffening sheaths not being available in prior art catheters;

(v) to provide a tamponade catheter which utilizes a bulbous or rounded exploring tip and further comprising a puncture resistant balloon, an inner protective sheath for the balloon, and an outer introducer sheath into which the inner sheath and catheter-balloon assembly fits such that the proximal portion of the outer exploring tip fits inside the outer stiffer introducer sheath to create a smooth junction between the outer exploring tip and the outer sheath to minimize wound insertion forces and prevent tissue damage during insertion; (w) to provide a tamponade catheter which utilizes a bulbous or rounded exploring tip attached to the distal end of the puncture resistant balloon catheter shaft, said catheter assembly having an inner sheath covering directly the balloon rolled or folded around the catheter shaft, and an outer sheath such that said catheter with its balloon and its balloon enclosing protective inner sheath can be extended through the distal opening of the stiffer outer sheath such that when the inner catheter assembly is extended, the protruding part instantly assumes a preformed slightly bent or curved shape, such that by rotation of the stylet by using the stylet handle on the proximal end, the bent portion of the catheter tip protruding from the distal end of the outer introducer sheath will orbit within the wound track to find the true wound track, but without true rotation of the inner sheath and balloon assembly which would wrap lose tissue about it if it rotated rather than orbited, such orbiting action of the extended catheter assembly through the distal end of the outer sheath will help to find the true wound track and follow such true wound track and thus assist insertion and navigation within the wound track to its terminus;

Other objects and advantages of the present tamponade catheter system invention and method of use will become obvious to the reader and it is intended that these objects and advantages are within the scope of the present invention.

To the accomplishment of the above and related objects, this invention may be embodied in the form illustrated in the accompanying drawings and that fully described in the text, attention being called to the fact, however, that the drawings and descriptive text are illustrative only of certain features of certain embodiments and that the functions and methods described and shown therein are, in many cases, achievable by alternative methods from those indicated for schematic and simplicity purposes. Further it is to be understood that some aspects of my invention are not specifically illustrated in the drawings, but that all aspects of my invention are fully described in the text such that one of ordinary skill in the art could, using such descriptions, practice my invention based on the written disclosure alone, or in combination with the drawings when appropriate.

SUMMARY OF THE INVENTION

The present invention provides a new internal compression catheter and method of use for treating internal hemorrhage from various wounds, particularly penetrating injuries from gunshot wounds, shrapnel wounds, and stab wounds.

BRIEF DESCRIPTION OF THE DRAWINGS

In the drawings, closely related figures have the same number, but different alphabetic suffixes.

1a shows a typical Foley urinary catheter which has been used to tamponade penetrating trauma.

1b shows a Cook Catheter "Liver Tamponade Balloon" designed to be inserted into penetrating liver wounds. The Liver Tamponade Balloon is silicon and, being of small volume when uninflated, generally conforms to the catheter before inflation.

1c shows the Cook Catheter "Kaye Nephrostomy" balloon catheter and stylet that is used for controlling hemorrhage from the nephrostomy wounds created at surgery for the removal of kidney stones.

Figure 1:
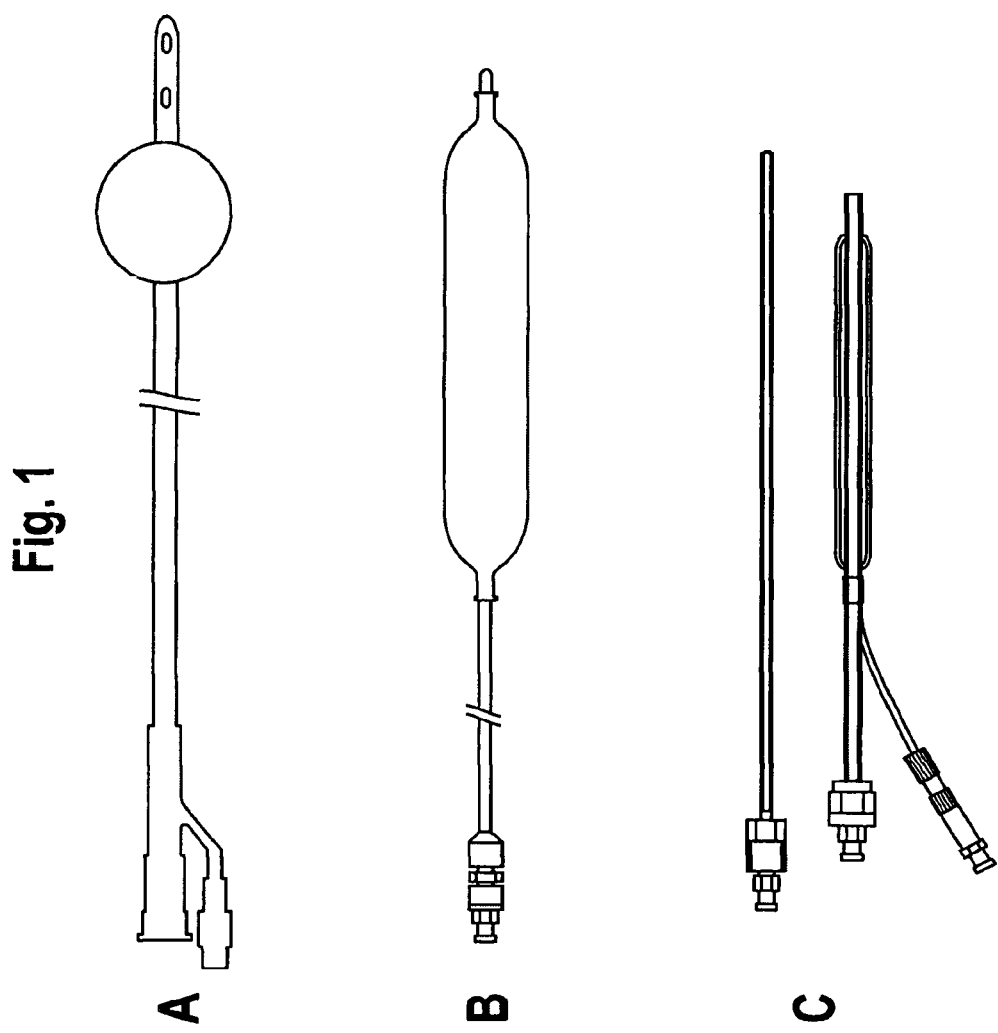
FIGS. 1a-1c shows three of the prior art devices used to tamponade hemorrhage of various types.
Figure 2:
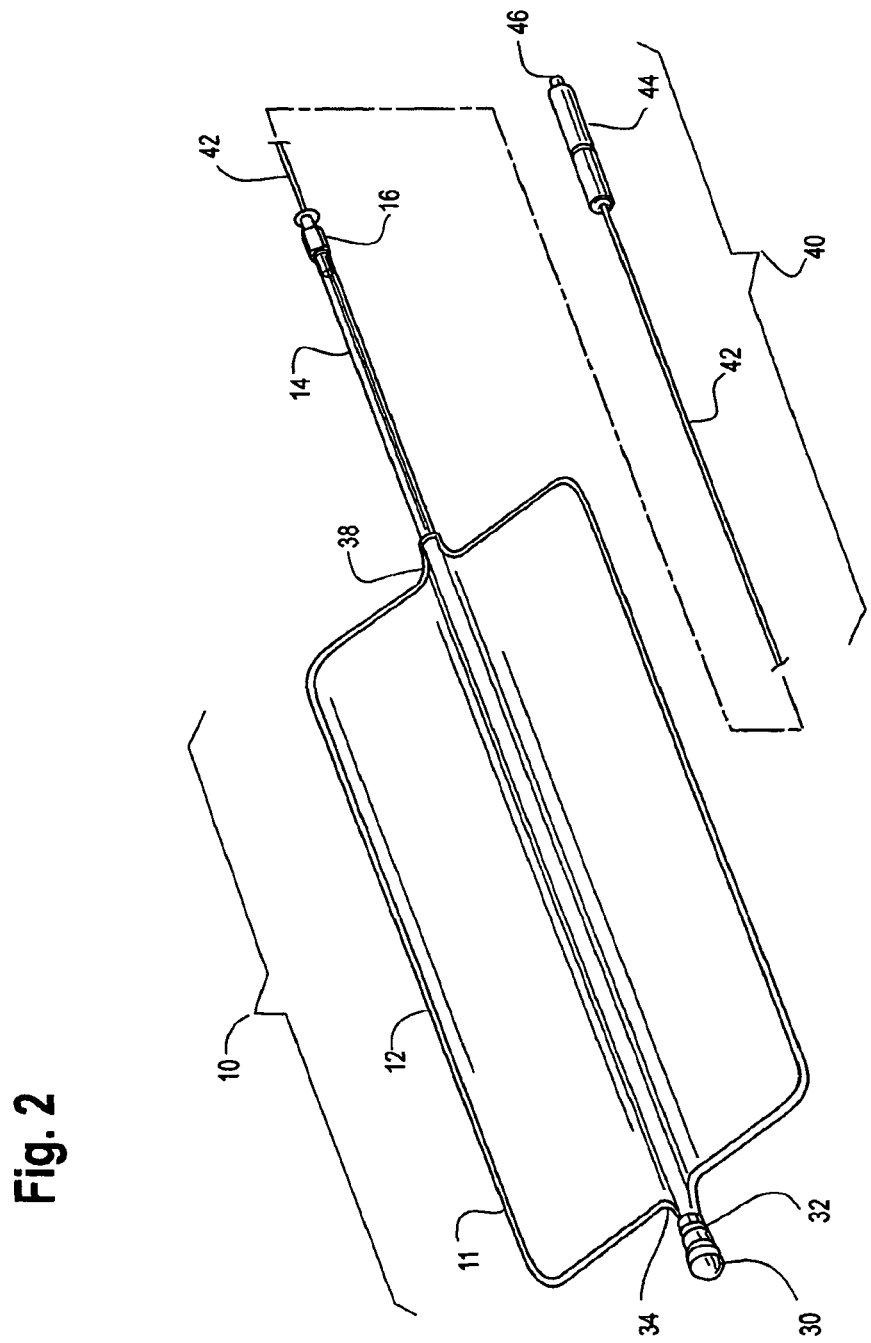

FIG. 2 shows the construction of the internal compression tourniquet catheter system, with the high volume, welded construction, nonelastic balloon fully deflated, and the inner stylet with handle used in the process of insertion and positioning within the wound track. The rounded outer and inner exploring tips are also shown as well as the Luer fitting used for inflation.

Figure 3:
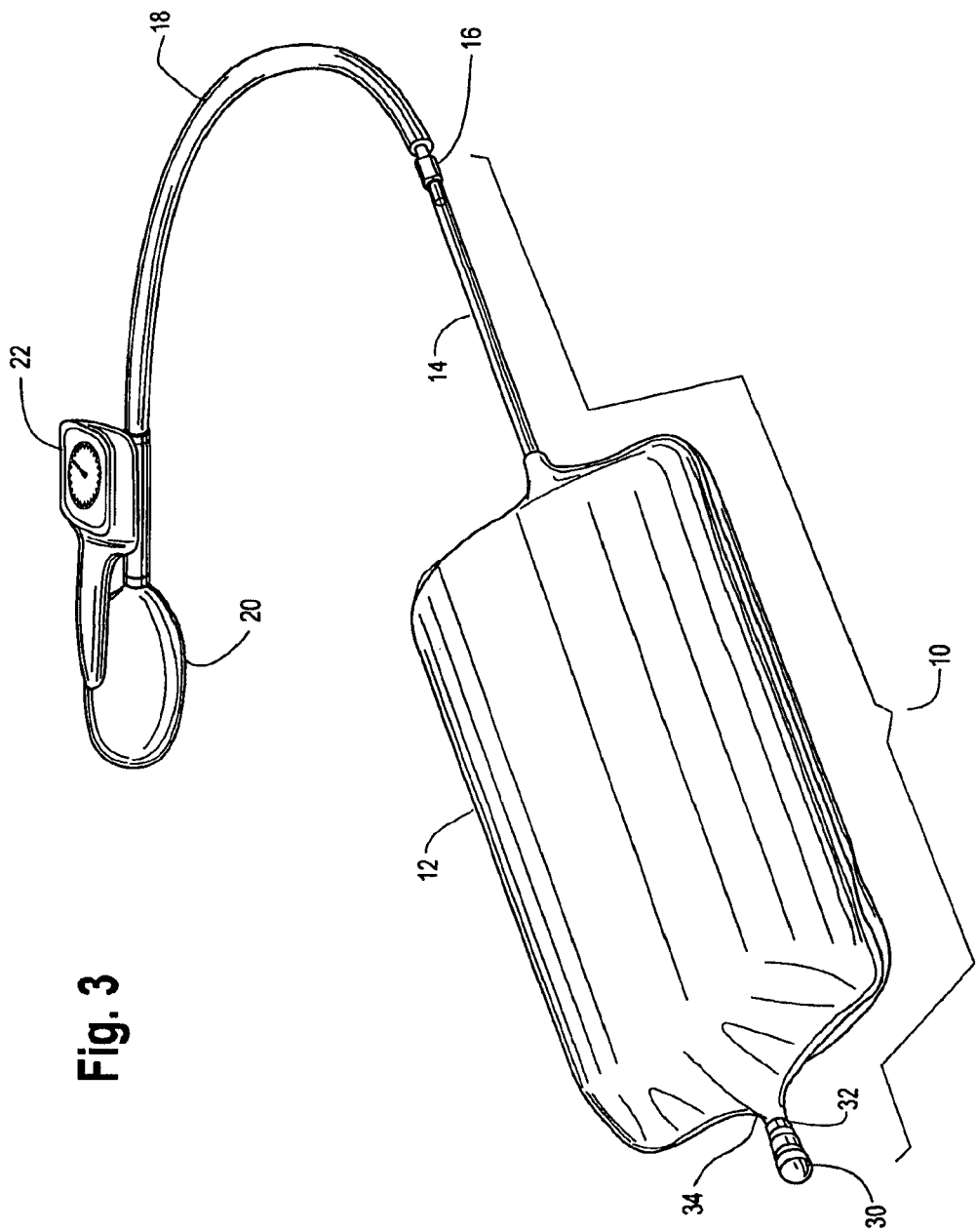

FIG. 3 shows the high volume, welded construction, nonelastic balloon partially inflated as used with the inventive balloon tamponade catheter system. The illustrated manually operated pneumatic bulb and pressure gage is one of several ways to inflate my inventive tamponade balloon catheter system.

Figure 4:
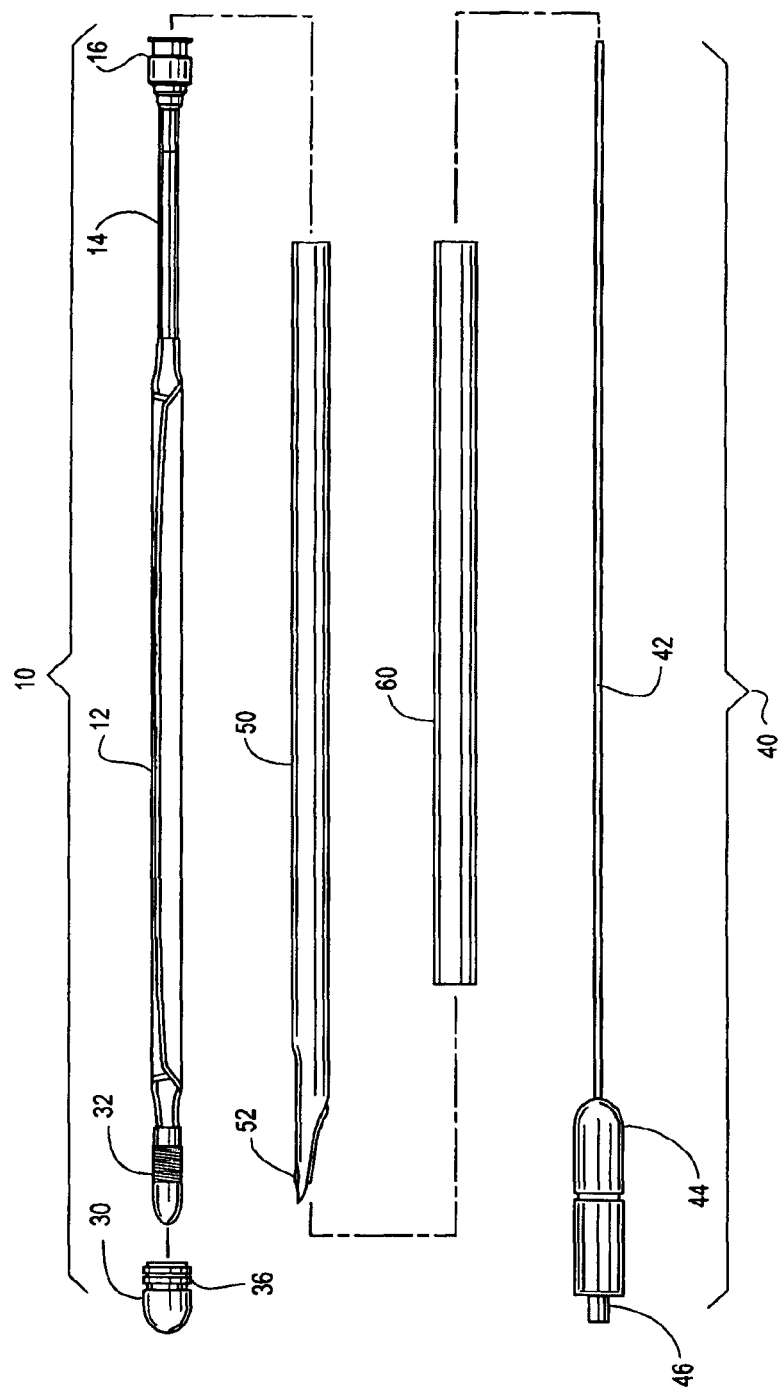

FIG. 4 shows the construction of the internal compression tourniquet catheter system with a bulbous rounded tip, the attached balloon wrapped snuggly around the catheter shaft, the inner sheath with pull tab, that inner sheath covering the wrapped balloon, the outer sheath which encloses the inner sheath and mates with the exploring tip, and the flush length stylet which is inserted into the catheter tube, and here shown straight before it is bent to cause deflection of the distal portion of the catheter assembly.

Figure 5:
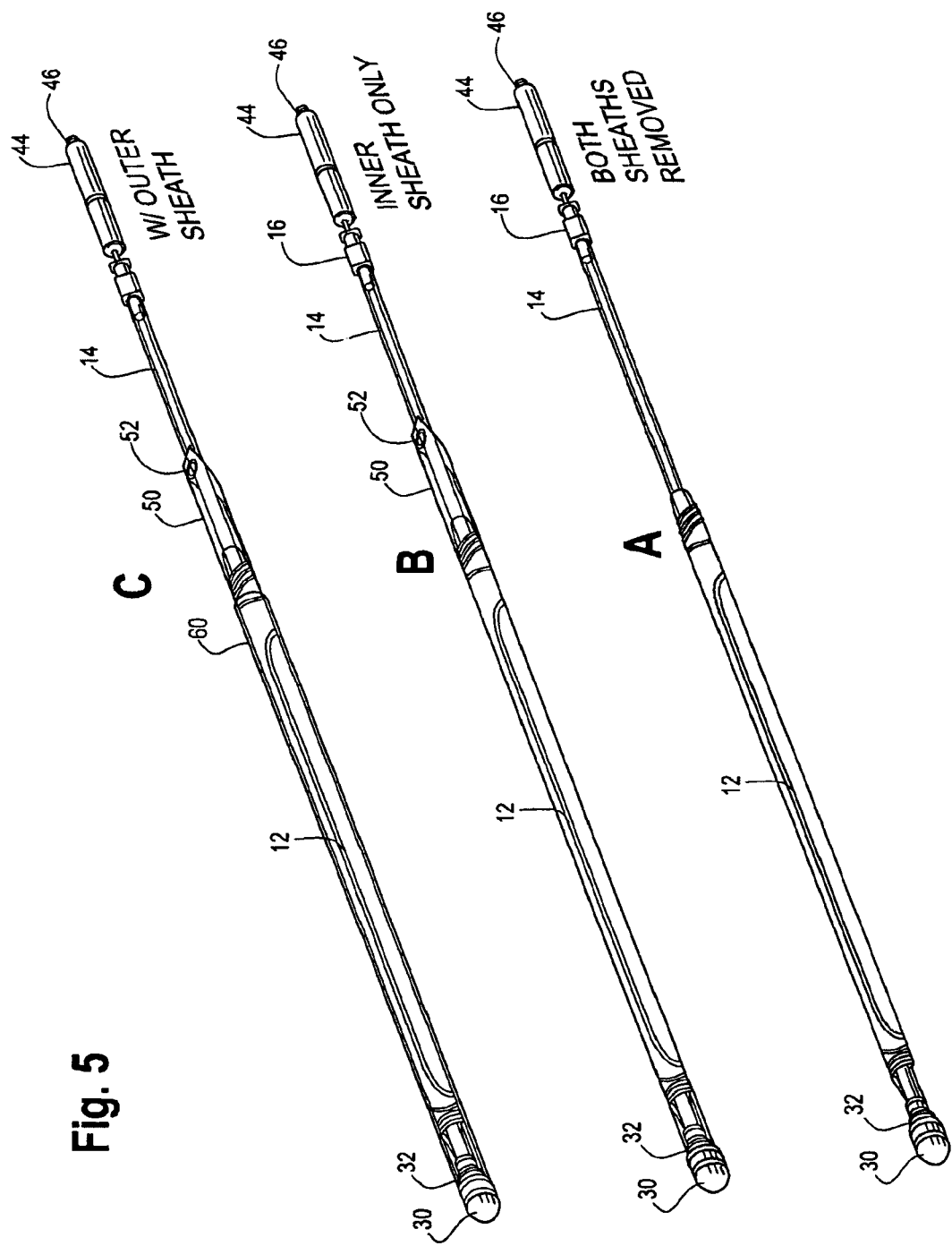

FIG. 5a-5c shows the inventive catheter in various phases of assembly during construction. The inserted stiffening stylet and handle are also shown in each of the figures and the inner smaller exploring tip has been secured to the distal catheter tip and the outer bulbous, rounded exploring tip is attached over the smaller inner tip of the catheter.

5a shows the catheter with the fully evacuated balloon wrapped around the catheter shaft prior to its insertion into the inner protective sheath.

5b shows the catheter as in 5a but after the rolled balloon and catheter assembly of 5a has been inserted into the inner sheath which then covers the tightly wrapped balloon.

5c shows the assembly of 5b now covered with the outer, stiffer sheath and ready for packaging and sterilization before insertion into a wound track.

Figure 6:
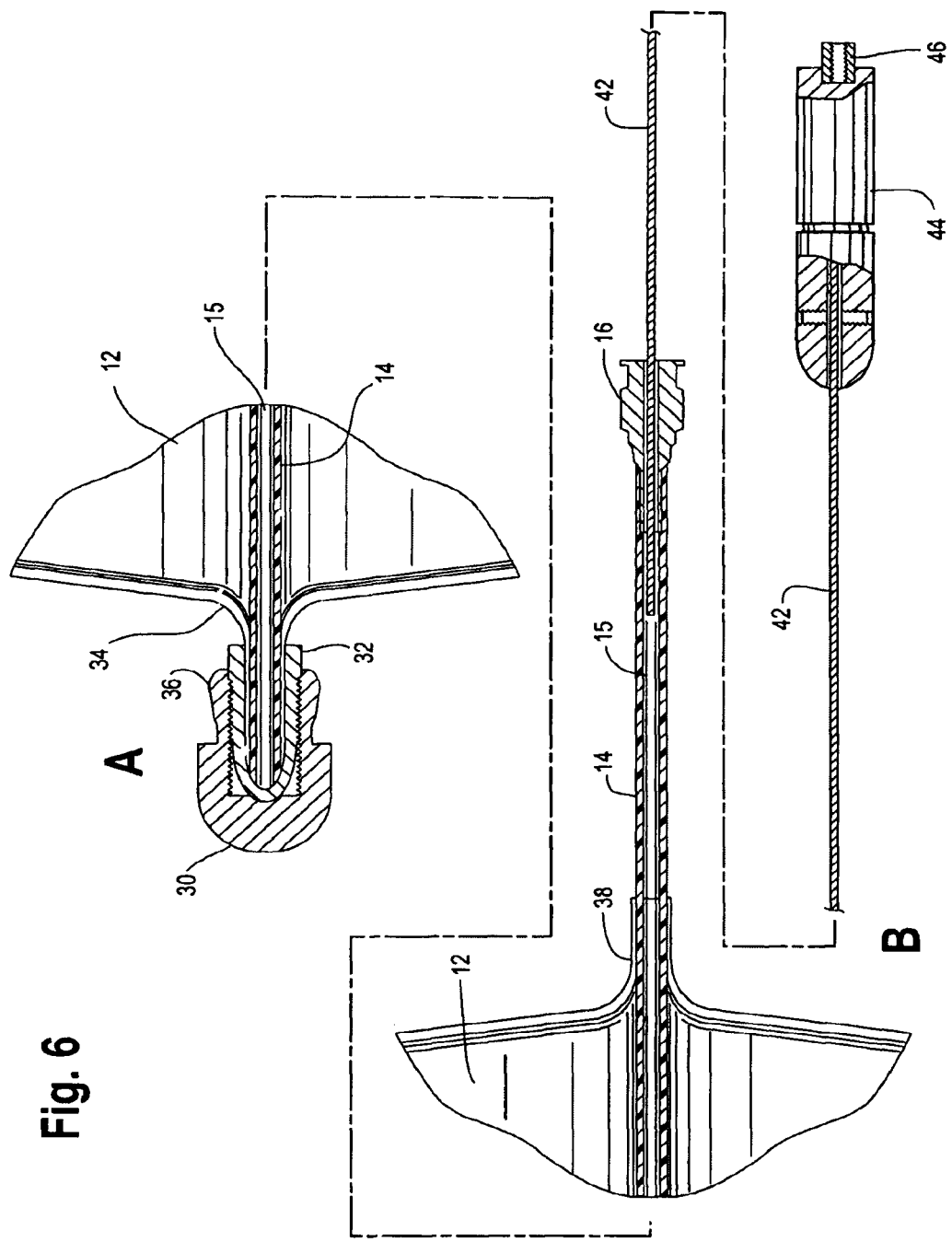

FIG. 6a-6b shows the detailed construction of the internal compression tourniquet catheter system exploring tip assembly and the stylet and its handle.

6a shows the inner, smaller exploring tip, and the outer, larger diameter exploring tip threaded over the inner exploring tip.

6b shows the proximal end of the catheter with its Luer fitting and the stylet with handle and hexagonal protuberance for engagement with the optional electrically powered stylet rotator.

Figure 7:
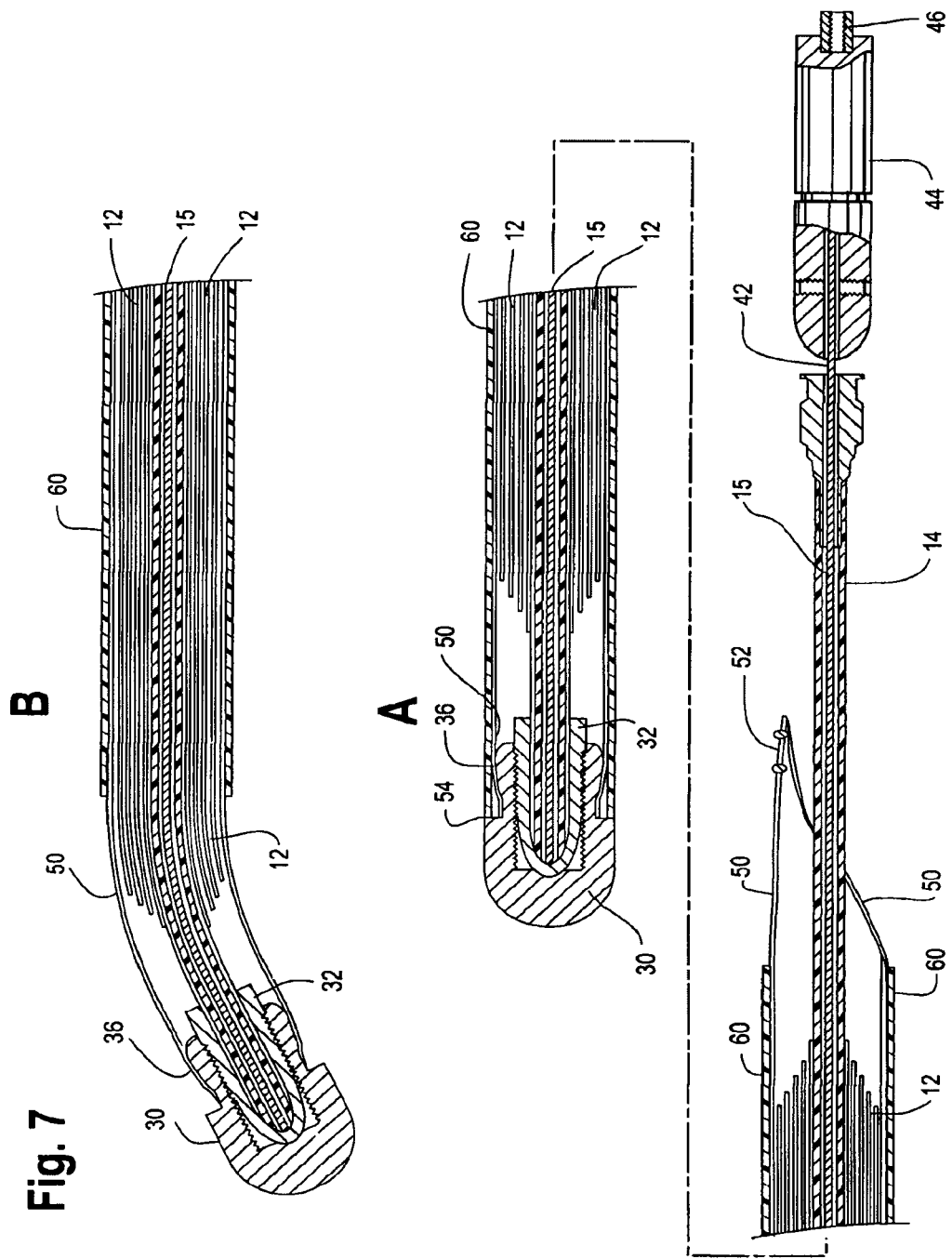

FIG. 7a-7b shows the detailed construction of the internal compression tourniquet catheter system.

7a shows both the proximal end of the catheter with the stylet handle and the proximal end of the two sheaths with the pull tab on the inner sheath the distal end of the fully assembled catheter showing the inner and outer exploring tips, the inner sheath shrink fitted to the smaller diameter proximal end of the outer tip, and the outer sheath engaging the same smaller, proximal end of the exploring tip.

7b shows the proximal end of the catheter assembly as in 7a but in this figure the distal portion of the inner assembly has been extended revealing the preformed curve, imparted by the stylet when not constrained by the outer sheath, designed for aid in wound track navigation.

Figure 8:
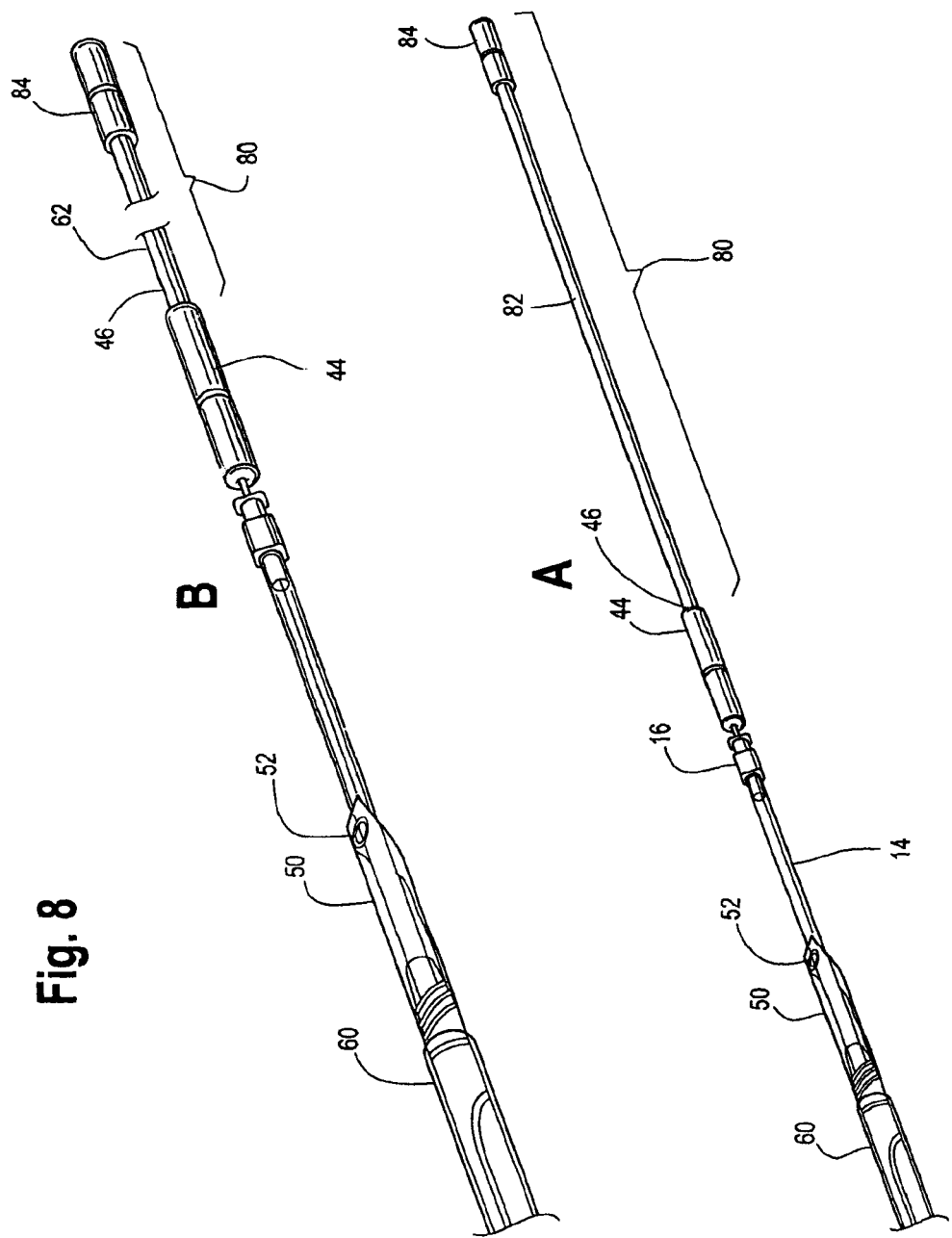

FIG. 8 shows the proximal end of the catheter assembly with attached stylet handle extension attached.

8a shows the proximal end of the catheter assembly before removal of the outer sheath and with the stylet handle extension attached to the stylet handle.

8b shows an enlarged view of FIG. 8a.

FIG. 9 shows the proximal end of the catheter and stylet handle with the electric rotator for automatic tip orbiting about to be attached to aid in wound track finding and following during insertion of the catheter.

FIG. 10a-10c shows wound track navigation using the pilot balloon wound tracking method with the extensible bulbous stylet embodiment where the wound is schematically represented by the curved dotted path.

10a shows the stylet is retracted and the pilot balloon deflated.

10b shows the stylet retracted and the pilot balloon for wound dilation is now inflated to open the wound.

10c shows the stylet is extended now into the opened wound track and the pilot balloon will then be deflated and the catheter advanced into the wound track over the now further advanced stylet.

DESCRIPTION OF THE INVENTION

A highly effective catheter system and method for controlling hemorrhage from traumatic wounds, particularly penetrating wounds, is described. Said system, referred to as an internal compression tourniquet catheter system, is constructed in the form of a catheter which has attached to a portion of its length an inflatable member resembling a balloon. Said inflatable member, the balloon, is constructed of nonelastic material such that when deflated it is flat and redundant around the catheter which passes within it. The balloon is nonelastic and is of large potential volume, and it can be inflated with near zero distending pressure and is such that when positioned within a wound track and inflated with gas or a liquid, the inflating pressure within the balloon is transmitted without diminution to the surrounding tissue of the wound track. Actually, due to the large volume, nonelastic construction of the balloon, it is the reaction of the tissues of the wound track to distention by the balloon that constrains the balloon inflation and thus creates pressure within the balloon. Thus, if 100 mmHg of pressure exists within the compression element balloon while the balloon is within a wound track, the tissue external to and in contact with the thus pressurized balloon will have exactly 100 mmHg of pressure exerted directly on it through the balloon membrane wall, since no pressure is consumed by inflation of the balloon within its volume limit. If there were no wound track to constrain the balloon inflation, there would be no pressure within the balloon during inflation until it reached its volume limit. Thus the pressure exerted on the tissue to tamponade the hemorrhage can be precisely controlled so that enough pressure is created within the tissue to tamponade bleeding, but not so much as to damage the tissue being compressed by the balloon. Similarly, since the balloon of the inventive catheter is very large, it can expand to compress small, large, and irregular wound track shapes to successfully tamponade wounds that smaller, compliant balloon catheters would be unable to tamponade. The material of the balloon is such that it is very thin so that the balloon can be rolled or folded about the catheter shaft which is typically about 12 French or 4 mm in diameter and thus not create a total catheter, balloon, sheath diameter of over 13 mm. It must also be very puncture and cut resistant to prevent inadvertent deflation during insertion or inflation by sharp bone shards, bullet fragments, r pieces of shrapnel.

The inventive catheter system and insertion method also includes one of several types of internal stylets to assist in wound track navigation of the device, said stylets being either of the same length of the catheter and flush with the distal catheter tip. The distal catheter tip is optimally bulbous or rounded, such bulbous shaped catheter tip being specifically shaped to prevent snagging or hanging-up of the catheter on the tissues of the wound track during insertion fully into the wound track until reaching its terminus.

Alternatively, as in a slightly different embodiment, the stylet may be with a shaft length that is longer overall than the catheter shaft and can thus can be made to protrude several inches further than the distal tip of the catheter by pushing this longer stylet distally using its handle. This longer stylet is in this embodiment fitted with a bulbous tip to facilitate the insertion of the stylet into the wound track during the insertion process and the catheter is then advanced over the previously advanced stylet in order to navigate completely the wound track to its terminus. In both embodiments however, the tip of the stylet can be bent slightly to facilitate following a curved or irregular wound track and the stylet handle is such that it allows rotation of the stylet and provides an indication of tip bend orientation by tactile feel of the stylet handle, or by visual sight of the handle of the orientation indicator on the stylet handle.

In the preferred embodiment, the stylet is fully enclosed except for its handle within the catheter, and is preformed to have a curved distal tip. However, when the curved stylet and catheter assembly is inserted into a stiff outer sheath, the sheath causes the stylet to straighten temporarily while the stylet-catheter assembly is so contained within the stiff outer sheath. However, if the stylet-catheter assembly is advanced several inches distally, and is thus protruding out of the distal end of the outer sheath, the preformed stylet bend is now unconstrained by the stiff outer sheath and hence the stylet-catheter assembly again assume a bent or curved shape which is often useful in "finding and following" the true wound track and hence permitting complete wound track navigation all the way to the track terminus or to its exit wound through the skin.

This ability to find the true wound track is important since the tamponade action of the catheter's inflatable member may not be effective if it is not positioned completely within the wound track. In one method of insertion, to assist in finding the true wound track, the stylet handle is attached to a motorized rotator to rapidly rotate the stylet within the catheter and hence cause the catheter tip to orbit (not rotate) within the wound track, such orbiting being in some cases an assistance to the insertion of the catheter assembly and its navigation of the wound track to its terminus. Under most circumstances however, the rotation of the stylet to find the wound track, if required, is done manually by twisting with the fingers of one hand while the other hand directs the outer sheath, and hence the enclosed catheter with its rounded or bulbous exploring tip, into the wound track. This is a new method of catheter insertion not possible with prior art catheters.

In another embodiment, one in which a bulbous tipped stylet as previously described, protrudes moveably from either end of the catheter, it is possible, as a further enhancement to wound track navigation, to create a wound track dilating pilot balloon at the tip of the catheter to dilate the wound track as an aid to catheter navigation of the wound track. This is achieved by pulling the protective balloon sheath proximally to uncover the distal inch or two of the balloon and then inflating the unconstrained distal portion of the balloon. Thus, when inflation pressure is applied to the balloon through the balloon inflation port, only the distal portion inflates which functions as a wound track dilating pilot balloon which then allows the advancement of the bulbous tipped extensible stylet further into the wound track ahead of the distal end of the catheter. After said stylet is further advanced into the wound, the pilot balloon may be deflated (though often not necessary to do so) and the catheter assembly is advanced over the stylet until it is stopped by the bulbous tip on the stylet. The pilot balloon is again inflated (if previously deflated), dilating the wound locally, and the stylet is again advanced further into the wound track. This pilot balloon assisted "wound tracking" method is repeated until the catheter is at the terminus of the wound track or exits the exit wound at the skin at which point the sheath is removed from the rest of the balloon and the thus the fully exposed balloon is then inflated to effect tamponade and hemorrhage control. Even though the balloon is constructed of puncture resistant material, if there are sharp fragments at the entrance of the wound, it may be advantageous to further protect the integrity of the balloon and retain the protective function of the balloon sheath over that small proximal length of catheter that is exposed to such sharp fragments to prevent inadvertent puncture of the balloon.

Once the catheter is positioned fully within the wound track, inflating pressure is applied by any of several means to the Luer fitting on the catheter to inflate the balloon. Once the pressure is created within the catheter, by any of the possible means, such pressure must be retained within the system by use of a seal or plug of some type at the Luer fitting, such seals being at least one of a stopcock, a plug, a check valve, or the like. In most embodiments of my system, such devices are included as a part of the system so that the user does not have to find such sealing means themselves.

Returning to means for inflation of the tamponadding balloon, one such inflation method is to pump air into the tamponade balloon with a hand bulb attached to the catheters Luer fitting (such hand bulbs are often used for measuring blood pressure and hence are readily available). Such pressurization of the balloon should be to a specific, desired pressure as indicated on a pressure gauge attached to the inflation line In most circumstances the desired pressure level is recommended to be between 60-150 mmHg depending on the tissue type, the level of patient's blood pressure, and the demonstrated effectiveness of various levels of inflation pressure on tamponadding the bleeding successfully in each patient. Such pressure should be set and then periodically checked to assure that the desired level of pressure I maintained. This checking process typically involves reattaching the pressure gauge to the Luer fitting or to a stopcock attached to the Luer fitting and reading the retained pressure level on the gauge.

In an enhanced catheter construction that includes an additional small external pressure indicator balloon that is subjected to the same pressure as that inflating the tamponade balloon, the pressure can be estimated by manual feel of the hardness of this small external indicator balloon. Similarly, an enhanced catheter system may be fitted with a small direct reading pressure gauge, or indicator, that will at all times indicate the level of pressure within the balloon and hence warn of too high or too low pressures within the tamponadding balloon within the tissue space.

Another device and method for the setting and following of the pressure within the tamponade balloon is to utilize an electronic module that incorporates a pressure transducer means that will measure and indicate the pressure to the user, and which will visibly and audibly alarm if the desired, and previously set, pressure is at substantial variance with the current pressure within the system. In a further enhancement to this electronic measurement and indicator system, the system could be equipped with an electronic pressure release valve and a very small air pump to constantly and automatically maintain the pressure within the balloon at the desired level, alerting when major adjustments are required since such required adjustments may indicate a leak in the balloon. This automatic control mechanism is particularly desirable when my catheter system is to be used for many hours and when the presence of trained personnel will not be constantly in attendance. These circumstances will often occur during prolonged transport of wounded personnel. They also occur in the hospital setting prior to and after surgery where my tamponadding system is used to stanch or prevent bleeding either by application within a traumatic wound track or its application at surgery as a wound packing device and method, in place of the traditional gauze packing, to maintain abdominal or thoracic pressure for control of hemorrhage.

The aforementioned aspects of my invention related to pressure control are suitable in many circumstances where they may be available, but in some circumstances, such as battle wounds or hunting accidents it is advantageous to be able to inflate the system with minimal equipment since the optimum inflation equipment may not be available. The simplest way to create pressure within the balloon is for the user to blow into the system using a small tube attached to the Luer fitting or the stopcock. A typical human can create 80-100 mmHg by blowing into the tube and using their lungs to start the process and transfer the majority of the air needed to pressurize the system, and then using their cheeks like a trumpet player to create the final higher pressure needed for successful tamponade.

Another method of inflation of the compressive balloon, which has many advantages over gaseous compression is to pressurize the balloon by injecting saline, or other liquid such as plain water, rather than using a gas as just described. The use of a liquid to pressurize the system prevents any chance of air embolism should a leak develop in the balloon, and said liquid will leak out of the balloon much more slowly, in the event of a balloon puncture does occur, than a gas will leak out. The liquid also removes any pressure maintenance problems associated with air evacuation in un-pressurized flight over 2000-3000 feet. However, just as with gaseous inflation, the liquid pressure should be measured to assure that proper compressive pressure is applied to the tissue, either with an external pressure indicator or the small external pressure indicator balloon. When possible, it is optimal to pressurize the balloon with saline or water using an IV administration system whereby the balloon is pressurized by hanging the vessel of liquid at a level sufficiently high above the balloon to create the desired pressure distending pressure. This method has the advantage that once the balloon is pressurized with the fluid from the vessel, any leaks will be filled by the flow of additional fluid into the balloon and such leaks will be know to the user since there will be drops falling in the administration set drip chamber, just as in a typical IV fluid administration process where drops are counted to estimate flow rate of the fluid administration.

DETAILED DESCRIPTION OF THE PREFERRED EMBODIMENTS

Turning now descriptively to the drawings, FIGS. 1-10, in which similar reference characters denote similar elements throughout the several views and schematics.

Referring now specifically to FIG. 1a-1c, which is an external view of various types of prior art devices designed as, or used as, internal compression for hemorrhage control.

FIG. 1a shows a typical Foley urinary catheter which sometimes has been used in emergencies successfully, and sometimes not successfully, to tamponade bleeding from penetrating trauma. The use of this catheter for wound tamponade has several disadvantages as compared to my invention. Primarily, the deficiencies are that it uses an elastic balloon of spherical shape and small volume, roughly 30 ml. It is designed for insertion into the urinary track and hence has no means for insertion into a wound track. Both of these deficiencies make it substantially less effective than my inventive internal compression tourniquet catheter system since it is difficult to insert, has a small, spherical balloon which requires pressure to inflate and hence does not permit knowledge of applied balloon pressure to the wound track. This combination of deficiencies prohibits both reliable introduction and effective and safe tissue tamponade.

FIG. 1b shows a Cook Catheter "Liver Tamponade Balloon" designed to be inserted into penetrating liver wounds. The use of this catheter for wound tamponade has several disadvantages as compared to my invention. Primarily, the deficiencies are that it uses an elastic balloon of cylindrical shape, the balloon is effectively forced by its design to be a cylinder when pressurized and hence cannot conform to irregularly shaped wound tracks. Additionally, it is of small volume, roughly 60 ml. when fully inflated. Like the Foley in FIG. 1a, this prior art balloon is elastic and conforms tightly to the catheter shaft when not inflated and therefore requires pressure to inflate it, even when it is unconstrained. This property also forces it to be largely a cylinder and to not be able to fill all tissue voids that are of various diameters in the wound track. Such variation often being caused by yaw ("tumbling") of a missile as it passes through tissues. Additionally, the elastic balloon of the Liver Tamponade Balloon is not puncture resistant and is tightly stretched when inflated and hence will likely fracture if it comes in contact with any of the sharp objects (bone chips, bullet fragments, and shrapnel) found in the wound tracks of many ballistic injuries. The large potential volume of my non-elastic balloon does not suffer from these limitations, i.e. it is nonelastic, not stretched tight when inflated, and is puncture resistant. Hence, by system can provide a uniform pressure field within the varying diameter wound track which is sufficient for tamponade of large volume wounds. Additionally with my catheter system, said distending pressure can be precisely controlled by direct measurement and hence limited to a level of effective tamponade without the risk of injury to the tissue.

Another deficiency of this prior art device for tamponade of hemorrhage in the liver is that it has no introduction system (stylet, exploring tip, protective sheath, stiffening sheath, etc.) since it is designed for insertion into a well defined wound track in the liver. Hence, it has no means for effective insertion into less well defined wound tracks in tissues other than the liver.

All of these deficiencies make this prior art device substantially less effective than my inventive internal compression tourniquet catheter system, since the Liver Tamponade Balloon is difficult or impossible to insert into many wounds, has a small diameter, cylindrical, non-conforming balloon which requires pressure to inflate when unconstrained, and hence does not permit knowledge of amount of the pressure within the balloon that is actually applied to the wound track. This combination of deficiencies prohibits both the reliable introduction and the effective and safe tissue tamponade in most tissues other than the liver. Conversely, my internal compression catheter can be used in small and large wounds that are regularly or irregularly shaped and directed, provides the ability to know precisely the pressure applied to the tissue surrounding the wound track, and can be used safely in the liver as well as in other tissues, since it has an effective introduction system and a large potential volume.

FIG. 1c shows the Cook Catheter "Kaye Nephrostomy Catheter" and stylet. These catheters are used for controlling hemorrhage from the small nephrostomy wounds created at surgery for the removal of kidney-stones, in a procedure referred to as a percutaneous nephrostomy. Tough effective in this small, intentionally surgically created wound in the kidney, the Kaye balloon catheter is not designed for, nor is it effective for, tamponadding hemorrhage from most traumatic injuries, since it suffers from most of the same deficiencies of those prior art devices shown in FIG. 1a-1b, namely a very small volume, not puncture resistant, and the lack of a general purpose introduction system suitable for use in gunshot and shrapnel wounds.

FIG. 2 shows a perspective view of several of the components of one embodiment of my invention. In this figure, the tamponade catheter assembly 10 has been removed from its wound track insertion system, its stylet 40, has been removed, and its balloon 12 is fully deflated. Notice that when deflated the balloon is clearly of large potential volume, but when not inflated, it lies flat and is suitable for rolling or folding around the catheter shaft 14 to minimize the deflated size. This minimization of size of this large potential volume balloon is important since otherwise the bulk of such a large potential volume balloon would create a large diameter assembly and provide too much bulk and insertion resistance, thus making introduction fully into the wound track difficult or impossible.

The balloon is constructed of a thin, flexible, but non-elastic, and puncture resistant material such that it can be rolled into a small diameter around the catheter shaft and such that when it is pressurized, all of the pressure created within the balloon 12 is a result of the wound track constraining the expansion of the balloon. It is advantageously formed by creating peripheral seems 11 using heat sealing or RF welding two sheets of the chosen material into the desired shape and volume. Since it is a non-elastic balloon 12, injection of an inflating medium such as air, $CO_2$, oxygen, nitrogen, or water or saline, requires essentially no pressure to expand the balloon to its maximum potential volume. Since this is true, as long as the potential volume of the balloon is larger than the potential volume of the wound track, any positive pressure created within the balloon is a result only of the constraining pressure of the wound track tissue pressing against the balloon and resisting its inflation. In this way, the user can know precisely the pressure being applied to the wound track tissues and effect optimum tamponade without injuring tissues. Thus, in summary of this important difference between my device and prior devices is this property my balloon: the balloon is of very large potential volume, constructed of nonelastic material, and not like prior art balloons which are elastic and which conform to the catheter shaft when deflated and which therefore require pressure to inflate, even when unconstrained. Because of this, many wound tracks will be of such volume that the small volume of prior art devices will not expand sufficiently to tamponade the bleeding and if the wound track is small enough to be compressed by the low volume prior art balloons, it is then impossible to easily determine the actual pressure applied to the walls of the wound track since pressure is required to distend these prior art balloons even when unconstrained.

Continuing with the description of the embodiment shown in FIG. 2, The stylet assembly 40 is an important part of the introduction system and comprises the stylet shaft 42 which extends from the Luer fitting 16 at the proximal end of the catheter shaft 14 through the internal opening of the catheter shaft 14 all the way to the distal end of the catheter shaft 14 to the inner exploring tip 32, which is in this figure covered by the outer exploring tip 30 which is attached to the inner exploring tip 32 using mating threads on 20 and 32. In use, the Luer fitting will usually have a check valve or a stopcock attached to it to aid in the inflation and pressure maintenance process. In one embodiment, such devices are a permanent part of the catheter.

The stylet handle 44 has at least one means for the user to be able to determine, both visually and by tactile sensation, the rotational orientation of the stylet 40, and hence the tip of the stylet and catheter if the stylet is bent at its distal end 34. That is, if the tip is bent, knowing the rotational orientation of the stylet handle 44 provides similar knowledge of the exploring tip's 30 orientation such that the direction of the curve of the catheter's distal tip (FIG. 7b 50), which exists when the distal end of the catheter is extended a few inches from the stiff outer sheath (FIG. 7b 60), can be determined by the rotational position of the stylet handle. This knowledge of the rotational positioning of the stylet is useful during insertion of the catheter assembly into wound tracks that are irregular or substantially tortuous or greatly curved in their path through the body tissues of the trauma victim. The indicating means on the stylet handle can be one or more of a variety of well known indicating means, including a flat surface and/or a raised surface texture or a ridge on the handle 44 such that it is obvious to both tactile sensation and visual inspection the current rotational position the stylet handle, and hence the orientation of the bent catheter tip and its exploring tip 30 and or 32.

There is additionally an hexagonally shaped small protuberance 46 on the proximal end of the stylet handle 44, said hexagonal protuberance 46 being used alternately and optionally for, 1) attachment of an electrically powered stylet rotator (FIG. 9 90) sometimes useful in navigating tortuous wound tracks, or, 2) the attachment of a stylet extender (FIG. 8 80) useful for the removal of the external sheath after insertion of the catheter assembly into the wound track. Without the extension (FIG. 8 80) in the preferred embodiment, the user would risk catheter removal during the removal of only the outer sheath, or, to prevent such possibility the catheter shaft 14 would be required to be substantially longer to allow the removal of the stiff outer sheath (FIG. 4 60) once the catheter assembly is in place within the wound track and before inflation of the balloon 14. Thus, the use of the stylet extender 80 permits safe removal of the outer sheath and allows the catheter shaft to be substantially shorter which permits compact packaging suitable for carry in a soldiers rucksack. Prior art devices, though they have no sheaths to be removed, are regardless long and not suitable for such rucksack carry. Since my system is designed to save soldiers lives on the battle field, such design for compact packaging and convenient carry are imperative. Using this design the overall length of the catheter when packaged can be under 12 inches. In contrast the "Liver Tamponade Balloon" is approximately 20 inches when packaged.

The invention embodiment shown in FIG. 2 is one in which the inner exploring tip 32 is permanently attached to the distal end of the catheter 34 by any suitable gas tight means, such as friction, integral molding, adhesive, or other such attachment means and the outer threaded surface of 32 provides a means of removable attachment for the outer exploring tip 30, details of which are better seen in FIG. 6a. Similarly, the balloon 12 is attached to the catheter shaft 14 at the proximal 38 and distal 34 ends using such suitable means mentioned above for attaching the inner exploring tip to the distal end of the catheter shaft 14.

FIG. 3 shows a perspective view of the same embodiment of my invention as shown in FIG. 2. As in FIG. 2, in FIG. 3 the tamponade catheter assembly 10 has been removed from its wound track insertion system, its stylet 40 has been removed, and its balloon 12 has been partially inflated using the hand bulb 20 with integral pressure gauge 22 which is connected to the Luer fitting 16 on the proximal end of the catheter shaft 14 by the inflation hose 18 and a mating Luer fitting. As detailed before, the design of my tamponade balloon is such that it takes essentially no pressure to inflate the balloon to this partially inflated (or to even its fully inflated) condition unless the balloon is constrained externally such as it is when it is inflated while deployed into a wound track within an injured person. In this circumstance, the tissues comprising the wound track, and those tissues adjacent to the wound track, constrain the inflation of the balloon and cause the volume of liquid or gas injected into the balloon to produce a positive pressure within the balloon, and such pressure level in the balloon is also present in the tissue of the wound track. The injection of the same volume of liquid or gas into the balloon when the balloon is not constrained will result in essentially no pressure increase within the balloon.

The embodiment in this figure is the same as in FIG. 2 in which the inner exploring tip 32 is permanently attached to the distal end of the catheter 34 by suitable means. The outer exploring tip 30 is attached to the inner exploring tip 32 by suitable means, in this case, by threaded attachment. The base of the inner exploring tip 32 can be seen at the base of the outer exploring tip 30 and where it is attached to the distal end of the balloon 34 where it attaches to the catheter shaft 14 at its distal end and forms a closed cap at the distal end of the catheter shaft 14. Other embodiments of my tamponade catheter, such as the one described in a FIG. 10a-10c, and somewhat different and have the exploring tip attached to the distal end of the stylet, in which case the stylet is longer than the catheter shaft and is designed such that it extends retractably out of the distal end of the catheter shaft 34 when advanced by pushing the stylet handle 44 towards the distal end of the catheter. In this second embodiment, the stylet and its attached bulbous tip, is retractably extensible out the distal end of the catheter for several inches which aids in wound track navigation, using the previously described "wound tracking" insertion method also illustrated in FIG. 10 in which the stylet is advanced first into the wound track and the catheter is then pushed over the previously advanced stylet which forms therefore a guide for the advancement of the rest of the catheter assembly further into the wound track.

FIG. 4 shows the major components of the same embodiment of my invention as shown in FIGS. 2 and 3 in a sequentially exploded perspective view. In this figure, the various components of the inventive catheter system are shown in a sequentially exploded form as if before assembly of the final catheter system. At the top of the figure, the catheter-balloon assembly 10 is shown before placement of the sheaths 50 and 60 and the stylet 42. In this figure the balloon 12 has been rolled around the 12 French (4 mm diameter) catheter shaft 14 into a tight roll to minimize the rolled diameter of the large potential volume balloon 12 around the catheter shaft 14. The length of the balloon in this figure is 8.5 inches and the fully inflated diameter is 2.50 inches.

Typically, for a 2.5 inch diameter fully inflated balloon, the diameter of the fully assembled catheter system, including the sheaths, is less than 0.5 inches in diameter. If thinner balloon material is used, larger balloons can be created with the same outside diameter. Smaller diameters are achievable if smaller balloon dimensions, or thinner material, are used. In the manufacturing assembly of the system, the inner thin cylindrical inner sheath 50 is positioned over the rolled balloon catheter assembly to protect it and contain it during insertion and is shown just below it in the figure. The thin inner protective sheath 50 is optionally perforated along its length to make removal easier in order to expose the balloon 12 once the catheter has been paced inside the wound track and it is time to remove the outer 50 and inner 60 sheaths. Total removal, or at least partial removal, of the inner sheath 50 is necessary in order to un-constrain the rolled balloon prior to its inflation within the wound track once the complete assembly has been deployed successfully within the wound track and assisted by the tab with a grip enhancing element such as a brass eyelet set into the tab and shown as 52. Other obvious grip enhancing elements could also be used, such as a ring or a thickened fold in the end of the inner sheath tab. The thicker outer sheath 60, if present, is always removed before balloon inflation as well.

Below the inner sheath 50 in the figure is the stiffer, thicker walled, outer sheath 60. The distal end of the inner sheath 50 is snuggly mated to the smaller diameter of the outer exploring tip 30 such that when the outer sheath 60 is positioned over the inner sheath and catheter assembly, and the smaller segment of the outer exploring tip 36, the outer sheath 60 and the larger diameter of the outer exploring tip are flush and present a smooth transition for minimizing resistance and preventing tissue trauma during catheter system introduction into the wound track. Close up details of this arrangement are better illustrated in the upper portion of FIG. 7a.

At the bottom of the FIG. 4 is the complete stylet assembly 40 previously described in detail. When inserted into the catheter through the Luer fitting 16 the distal end of the stylet extends all the way to the distal end of the inner exploring tip 32 and the length of the stylet shaft is such that the handle 44 rests at or close to the Luer 16, which in use often will have a check valve or a stopcock attached to it once the catheter has been placed within the wound track.

Another embodiment of my invention, which looks very similar to the one in FIG. 4, and includes a large outer stylet tip 30 and a smaller inner stylet tip 32 similar to that shown in FIG. 4. In the new embodiment however, the outer tip 30 is made of a frangible material such that it will fracture and drop away from the inner tip 32 if the stylet is pressed quickly inward in the circumstance of the outer tip 30 meeting an impassible tissue resistance while attempting to navigate a wound track. The fracture of the larger outer exploring tip 30 will expose the smaller inner tip 32 which, as can be seen in the figure, is shaped such that it has a sharp, but rounded tip, resembling the ogive of a 0.22 cal bullet. Such inner tip geometry has been experimentally demonstrated to be capable of penetrating muscle tissue with a modest amount of catheter or stylet force, but without piercing the larger arteries thus encountered in driving it through uninjured muscle, said arteries being deflected to the side by the rounded tip of the inner exploring tip 32 when being pushed forcibly through muscle where there is no wound track.

Therefore, if during attempted wound track navigation using this embodiment of my catheter system, it is impossible to advance all the way to the terminus of the wound track, the outer exploring tip 30 can be fractured and separated from the inner tip 32 by a quick, firm inward thrust of the stylet handle 44. Subsequently, the inner tip 32 with its rounded point can be driven further into the tissue that is outside of, but close to, the true wound track. When the balloon is subsequently inflated, the pressure field created within the true wound track and more distally within the newly created false track is capable of tamponadding hemorrhage from major vessels in close proximity to the new false track as well as the true wound track. Though this is a maneuver used only is desperate circumstances, this is an embodiment and a method that has been proven effective, like all the other embodiments and methods, in actual tests.

FIG. 5a-5c shows sequentially perspective views of the "build-up" of the complete catheter system of the same embodiment of my invention as shown in FIGS. 2, 3, and 4.

FIG. 5a shows the catheter with the balloon 12 rolled tightly around the catheter shaft 14. The distal end of the catheter shows the attached inner 32 and outer 30 exploring tips and the proximal end shows the Luer fitting 16 and the handle of the inserted stylet 44.

FIG. 5b shows the catheter as in FIG. 5a but with the addition of the inner balloon protective sheath 50 with its pull tab 52.

FIG. 5c shows the catheter as in FIG. 5b but with the addition of the stiffer outer sheath 60 which inter-digitates with the smaller diameter of the outer exploring tip 30 to form a smooth outer profile and smooth surface for easy introduction into the wound track. Thus, the complete system shown in FIG. 5c is ready for insertion in to the wound track, whereby the stiffer outer sheath 60 permits directing the exploring tip 30 into the true channel of the wound track by external manipulation of the tip by griping the external sheath and first directing the tip towards the wound track and ten pushing the whole assembly into the wound track until the end of the wound track is reached or the exploring tip emerges from the exit wound if there is an exit wound. For most wounds, this method of wound track finding and catheter system insertion is sufficient.

Method of Typical Use of My Catheter System for Control of Major Hemorrhage

In actual use in a wound, once the fully assembled catheter, appearing in FIG. 5c as it would when removed from its sterile packaging, is fully inserted into the wound track, the outer sheath 60 is removed proximally over the inner sheath 50 and, using the stylet extension (FIGS. 8a and 8b 80) which is previously attached to the hexagonal protrusion 46 on the proximal end of the stylet handle 44, the outer sheath is removed entirely using the extension to apply continued inward force on the catheter assembly so that it is not inadvertently withdrawn as the external sheath 60 is removed over it. Once removed, the external sheath 60 and the stylet extension 80 are no longer needed and are discarded. The inner sheath 50 is then removed by holding the catheter firmly within the wound using the stylet handle 44 to apply inward stabilizing pressure and pulling on the pull tab 52 of the inner sheath 50. During its removal, the inner sheath 50 is split along its longitudinal perforation if present and is totally removed and discarded typically though it may be only partially removed if a shallow wound results in some of the balloon being external to the wound track.

Once the outer 60 and the inner sheath 50 are removed as just described, one hand then stabilizes the catheter by grasping the external catheter shaft 14 and the other hand is used to withdraw and discard the stylet by pulling it out using the handle 44. The catheter is now ready for inflation using a gas or a liquid inflation system as previously described. Often it is advantageous to place a stopcock or a check valve on the Luer fitting 16 so that the inflation system, whether pneumatic or hydraulic, can be removed for convenience in transport and yet still maintain the pressure within the balloon, which as detailed earlier is also the actual pressure applied to the walls of the wound track and which is responsible for the tamponade of the bleeding in the wound track and the adjacent tissues.

Typically, the introduction of the catheter takes only a few seconds, but some wounds are particularly difficult to intubate and take substantially longer, up to several minutes. In any case, the inadvertent removal of a fully placed catheter must be carefully guarded against at each step of the tamponade catheter placement and sheath removal as the catheter is readied for inflation of the balloon, which is the last step in the catheter deployment and tamponade process.

Many times the exit wound, if present, will provide a better initial entry path for the catheter since the exit wound is typically larger in diameter than the entry wound. However, many penetrating wounds do not have an exit wound and the entry wound may be actually somewhat smaller in diameter than the catheter and introducer system. In this case, it will be necessary to slightly enlarge the skin wound by creating a small peripheral cut in the entry wound to enlarge it sufficiently to: 1) first admit an exploring finger to establish the direction of the wound track within the body so that the introduction of the catheter system will be in the proper wound track direction and 2) to permit the introduction of the catheter system into a wound track capable of admitting the catheter system generally, except for the restriction that a small skin entry (or exit) wound presents. Ballistic wounds typically have an entry wound that is smaller than the bullet that made the wound, often by as much as 50% smaller. The addition of the small cut to slightly increase the size of a small entry wound, typically not more than a ¼ inch cut being required, is exceptionally valuable in that the insertion of the catheter system is greatly facilitated by first establishing the direction of the wound track with the finger before directing the catheter into the wound track.

The above process and method are the process for insertion and inflation of the catheter system into a typical penetrating entry or exit wound. However, certain very small wound tracks will first require the removal of the outer sheath 60 and removal of the outer exploring tip 30 to thus provide a small diameter catheter system for navigation into wound tracks with very small diameters or those that pierce bones with a small, clean, un-fractured hole. Though not common, these small wound tracks require an introduction system that is capable of quickly, and without requiring any tools, being converted into a smaller diameter catheter system and my invention provides that capability by simply removing the outer sheath 60 by slipping it off over of the proximal end of the catheter, i.e., over the inner sheath 50 and the stylet handle 44 and then unscrewing the outer exploring tip 30 from the smaller inner exploring tip 32. When these actions are accomplished, one produces a substantially smaller diameter exploring tip and a smaller diameter catheter assembly which can be introduced into smaller wound tracks. Typical values for a size reduction are such that a normally 0.44 inch outer diameter catheter system will be reduced down to a 0.25 outer diameter system. If the wound track can accommodate the larger size, it is easier to navigate the wound track with the larger size, but if not, then a smaller diameter is essential.

It is important to note that, as a part of my method for arresting hemorrhage, in combination with my new internal compression catheter system, it is sometimes advantageous to introduce two catheters into a wound that is exceptionally large in diameter or exceptionally long in length. In the case where there is an exit as well as an entry wound, it may be useful to insert a catheter into each skin wound as far as possible and inflate both in an effort to most effectively tamponade bleeding. This is particularly true when it is not possible to get a single catheter introduced such that the single balloon length of the catheter is capable tamponadding the entire wound track length. In such cases, if an exit wound exists, it has been show to be advantageous to insert an additional catheter into that wound as well as the entry wound. Since the balloon inflation pressure is controlled in each catheter, the presence of two catheters, even if overlapping within the wound track, poses no hazard to tissue due to over pressurization since the pressure of each is precisely controlled.

Though the previous method description is that most often used for insertion and inflation of my catheter system for the control of severe hemorrhage, there are other, additional subtleties of the introduction process that may be useful in various circumstances and those will be further described as a part of the remaining figures.

FIG. 6a-6b shows detailed, close up views of the proximal and distal portions of the same preferred embodiment of my inventive catheter system as that shown in FIGS. 2, 3, 4, and 5.

FIG. 6a shows a close up view of the inner 32 and outer 30 exploring tips when they are in the standard position of having the outer tip 30 affixed over the inner tip 32, in this case using a threaded attachment. Also shown the proximal portion of the outer tip 30 is the smaller diameter portion 36 over which the inner sheath is shrunk tightly when the catheter is manufactured. The outer sheath 60 fits over this smaller portion 36 of the outer exploring tip 30 such that the larger diameter of the outer exploring tip 30 is of the same size as the outer diameter of the outer sheath 60. This relationship is even better illustrated in the upper portion of FIG. 7a. Notice that the central hole 15 in the catheter shaft 14 extends to the distal end of the inner exploring tip 32 and the stylet shaft 42 is designed to extend all the way to the end of the inner tip 32 within the central hole of the catheter shaft. This is important, since in the preferred embodiment, the stylet is preformed with a slight bend or curve at its distal tip and this will cause the distal portion of the catheter 34, including the exploring tips 30 and 32, to bend if the inner assembly is extended out the distal end of the outer sheath 60. While inside the outer sheath, the catheter assembly is maintained in a straight configuration due to the stiffness of the outer sheath (and the flexibility of the stylet shaft 42) which causes the stylet and catheter to assume a straight shape when constrained by the relatively stiff outer sheath 60. The assumption of a bend or a curve at the distal end of the inner catheter assembly when the inner assembly is extended a few inches is better illustrated in FIG. 7b.

FIG. 7a-7b shows detailed views of the proximal and distal portions of the fully assembled form of the same preferred embodiment of my inventive catheter system as previously shown in FIGS. 2, 3, 4, 5 and 6.

The lower portion of FIG. 7a shows the proximal portion of the tightly rolled (or alternatively folded) balloon 12, the inner sheath 50 with pull tab 52 used for its removal from around the balloon 12, and the outer sheath 60. Within the inner passage IS of the catheter shaft 14 is the stylet shaft 42 which is attached at its proximal end to the stylet handle 44 (illustrated using set screws but many methods of attachment will suffice) with its hexagonal protuberance 46 used for temporary attachment of either the electrically powered rotator (FIG. 9 90) or the stylet extension (FIG. 8 80) whose use was previously described.

The upper portion of FIG. 7*a* shows the distal portion of the catheter system and illustrates the placement of the inner sheath 50 which coven the rolled or folded balloon 12 and extends distally to mate with the smaller portion 36 of the outer exploring tip 30 to create a smooth junction at the shrink fit mating 36 which creates a joint that is separable by traction on 52 when the inner sheath 50 is removed by pulling on the inner sheath pull tab 52 before balloon 12 inflation takes place as the last step of catheter deployment for the control of hemorrhage. The outer sheath 60 perfectly fits over the inner sheath 50 and its junction to the outer tip at 36. The diameter of the larger outer exploring tip 30 is the same as that of the outer diameter of the outer sheath 60 so that a smooth junction 54 is formed where they meet. The stylet shaft 42 extends to the most distal part of the inner tip 32 and though the stylet has a preformed bend in the distal 2-3 inches, it is held straight until extended as shown in FIG. 7*b*, by the stiffness of the outer sheath as shown in the top portion of FIG. 7*a*.

FIG. 7*b* shows the distal portion of the catheter system in which the inner catheter assembly has been extended a few inches from the stiff outer sheath 60. When so extended, the inner catheter assembly assumes the bent or curved shape that has been previously formed in it, but which has been held straight by the constraint of the outer sheath 60. When extended in this way to produce a curved configuration to assist in finding the true wound track in a difficult wound such that it is not possible to find it with the catheter system in the straight configuration. Thus, the curved, extended portion of the catheter system is caused to orbit incrementally 360 degrees within the wound track by rotation of the stylet handle 44, to "search for and follow" the continuation of the true wound track. This tip orbiting feature and method, designed to help with difficult wound track navigation, is most often produced by manual rotation of the stylet handle 44 which is assisted by tactile sensation on the handle 44 for the operator to know in which direction the tip is pointing within the wound at each point of handle 44 rotation and before the required forward pressure to find the wound track. A series of partial rotations with forward pressure at the end of each partial rotation is often effective in finding and following a curved wound track. Though the manual rotation is generally sufficient to find the wound track, a rapid rotation may be produced by using the electric rotator (FIG. 9 90).

Once the curved tip of the inner assembly finds the true wound track and the catheter is advanced further into the wound track by inward pressure on the stylet handle, the outer sheath 60 is then advanced over the previously advanced inner assembly by grasping the catheter shaft 14 with one hand and advancing the outer sheath 60 inward into the wound track with the other hand to cover again the previously extended several inches and thus to re-assume the straight configuration shown in the upper portion of FIG. 7*a*. Experience has shown that approximately 20% of wounds will benefit from this tip orbiting capability during the process of wound insertion and full wound track navigation of the catheter system, prior to sheath removals and inflation of the balloon to the proper pressure to cause tamponade of the bleeding.

FIG. 8*a*-8*b* shows detailed views of the proximal portions of the same preferred embodiment as shown in FIGS. 2, 3, 4, 5, 6, and 7 of my inventive catheter system. In both portions of this figure the catheter system is shown with the stylet extension 80 attached.

FIGS. 8*a* and 8*b* show two views of the catheter system with the stylet extension 80 attached to the stylet handle 44 by tight friction fit over the hexagonal protrusion 46 on the handle's proximal end. The stylet extension 80 may optionally have a grasping handle 84 as well. This stylet extension 80 is made of a light material with sufficient rigidity to permit stabilizing the catheter assembly within the wound while the outer sheath is removed over the inner sheath 50, the catheter shaft 14, the Luer fitting 16, the stylet handle 44 and out over the stylet extension 80. When the outer sheath 60 has been removed from the catheter system sufficiently for its distal end to be proximal to the stylet handle 44, the stylet extension 80 is detached from the stylet handle hexagonal fitting 46 and both the outer sheath 60 and the stylet extension 80 are discarded since they are no longer needed. Although it is possible to remove the outer sheath 60 without the use of the stylet extension 80, experience has proven that it is risky to do so since without the stabilization of the stylet extension 80 to hold firmly the catheter system in the wound while the outer sheath 60 is removed, it is possible that the entire assembly will be inadvertently removed from the wound and necessitate a repeat of the entire insertion and wound navigation process over again, wasting valuable time and causing potentially fatal additional blood loss.

However, an alternative to using a stylet extension 80 to provide catheter system stabilization during the removal of the outer sheath 60 is to construct the catheter shaft 14 so that it is substantially longer than shown (overall shaft length in the figure is approximately 11 inches) which would permit stabilizing the catheter system in the wound using the stylet handle 44. With such long catheter shaft construction, one can remove the outer sheath 60 from the wound and over the proximal portion of the catheter shaft assembly by stabilizing the catheter by pressing in on the stylet handle 44 without the risks of un-stabilized removal of the outer sheath 60 that can result in inadvertent withdrawal of the catheter from the wound as described above. Regardless of the design approach that results in the desired stabilization of the catheter system within the wound while the outer sheath 60 is removed, once the outer sheath has been removed, it is discarded.

The process of removal of the inner sheath 50 necessary before balloon inflation also requires catheter stabilization to prevent inadvertent withdrawal from the wound. However, this stabilization can be done by applying manual inward pressure using the stylet handle 44 since the inner sheath is continuously stripped off to the side from the catheter shaft 14 as it is removed by pulling the tab 52 at an angle to the catheter shaft 14 and the enclosed stylet 42 which causes the inner sheath 50 to separate along the perforations along its length. Typically, the inner sheath 50 is totally stripped from the catheter and discarded prior to balloon, inflation although a small part of the inner sheath may be left covering the proximal portion of the balloon 12 if it is desired to prevent that portion of the balloon 12 from inflation as previously described.

Another embodiment of the outer sheath 60, designed to comply with the need for its removal without possible inadvertent withdrawal of the catheter assembly from the wound during the process, is to use with the outer sheath 60 the same approach just described for the construction and removal of the inner sheath 50. That is, by using a pull tab and long axis perforations (or a full length slit in the wall) for its removal off of the side of the catheter shaft 14 while the catheter assembly is stabilized within the wound by using only the standard stylet handle 44. That is, an alternative embodiment of the outer sheath 60 is a construction which includes a complete long axis slit, or perforations, that would permit its removal off the side of the catheter system shaft 14 in a manner analogous to the method of destructive removal of the inner perforated sheath 50 off to the side of the catheter shaft. This removal of the outer sheath 60 is in contrast to that earlier described using the stylet extension 80 as an aid and pulling intact the outer sheath over the proximal end of the catheter.

FIG. 9 shows detailed views of the proximal portions of the same preferred embodiment shown in the previous figures. In this figure is shown the previously described electric rotation device 90 used as a part of my inventive internal compression tourniquet catheter system. The rotation device 90 temporarily attaches to the stylet handle's 44 male gender hexagonal protuberance 46 which mates with a corresponding female gender hexagonal part 92 on the electric rotator 90. The rotator 90 has a there position control switch 94 which will, when manually depressed by the operator on its forward aspect will cause the device to rotate the attached stylet in a clockwise direction at a variable speed of 5-100 RPM. When the rear aspect of the rotator switch 94 is depressed, the attached stylet will rotate counter clockwise at 5-100 RPM. Other speeds are also achievable but these have proven most advantageous in electric rotation assisted wound navigation.

The rotation of the stylet by rotating its handle 44 using the electric rotator 90 mated temporarily to the hexagonal protuberance 46 causes the exploring tip to orbit (not rotate) within the wound track and by using gentle inward and outward pressure, while electrically rapidly orbiting clockwise and/or counter clockwise the extended, bent orbiting catheter tip in the wound, has been found to assist in wound track navigation in particularly difficult cases. Experience has shown that using the electric rotation device 90, (after previously using the previously described manual stylet handle 44 rotation and orbiting exploring tip 30 technique), as an aid in navigating a particularly difficult and tortuous wound track is required in less than 5% wound tracks navigated.

FIG. 10*a*-10*c* shows detailed views of another embodiment of my inventive catheter system in which the exploring tip is round and is attached to the distal end of the extensible stylet, rather than to the distal end of the catheter itself as in the previously described embodiment. The figure also illustrates the "wound tracking" method previously described as another method to assist catheter system insertion into a difficult to intubate wound track. In the figure, the dotted lines represent schematically the tissue walls of the hypothetical, curved, wound track 100 that is being intubated using the "wound tracking" method which is easily implemented using this extensible stylet embodiment.

FIG. 10*a* shows an embodiment of my inventive catheter system that uses a longer stylet 142 that freely passes through the center lumen of the catheter, said center lumen passing without obstruction from the proximal through the distal open end 115 of the catheter. This is in contrast to the previously illustrated catheter embodiment in that in the previously illustrated embodiment, the central lumen accommodated the stylet but the lumen was closed on its distal end by the inner 32 and outer 30 exploring tips and in which the length of the stylet shaft 42 was exactly equal to the length of the center lumen 15 of the previous embodiment such that the tip reached all the way to the distal end of the inner exploring tip 32 and could cause it to orbit if the inner assembly was extended and the stylet handle rotated as previously described.

In contrast to the previously described embodiment, in the embodiment shown in FIG. 10, the stylet shaft 142 is approximately 3-6 inches longer than the catheter's overall length and hence, using the stylet handle at the proximal end of the stylet (not shown in the figure), the user can extend or retract the stylet shaft 142 and its bulbous exploring tip 130 such that the bulbous tip is projected outward and into the wound track and away from the distal tip 115 of the catheter. The distance of this outward projection of the exploring tip 130 beyond the end of the catheter tip is user controlled, where the distance is variable up to the extent of the stylet's length that is in excess over the length of the catheter shaft itself. The stylet shaft 142 is free to rotate within the lumen of the catheter in an analogous manner to the stylet rotation described in the previous embodiment by using the stylet handle with manual rotation or using the electric rotation device 90.

Looking still at FIG. 10*a*, there is a retractable balloon protective sheath 150 with a pull tab 152 to aid its full or partial removal as desired by the user. In FIG. 10*a*, the sheath 150 is shown partially retracted such that a portion of the balloon 112 is exposed to the wound track 100. There are also one or more balloon 112 inflation lumens 151 which are separate and distinct from the central lumen of the catheter in which the stylet 142 passes. These balloon inflation lumens are connected to suitable connection fittings on the proximal end of the catheter for attachment of the inflation device as previously described, and they are made contiguous with the lumen of the balloon 112 by holes or other such passages from the inflation lumens into the lumen of the balloon and through which gas or liquid is passed during the balloon 112 inflation process.

Towards the distal tip 115 of the catheter, there is a small segment of stiff tubing 113, metal hypodermic tubing being one such material, placed or formed within the central lumen of the catheter and through which the stylet 142 passes and which has the function of maintaining a straight shape of the stylet shaft 142, which has a preformed bend or curve at its distal end. Thus, when the stylet is fully retracted such that the bulbous stylet tip is adjacent with the catheter tip 115 as shown in FIG. 10*a*, the stiff tubular segment 113 causes the stylet curve to straighten, hence resulting in a straight catheter assembly. During the insertion of the catheter system into a wound, a straight catheter is often preferable to one with a curved tip, and at other times, a curved tip is preferable. This design providing the option for both.

Directing our attention now to the hypothetical wound track 100 represented by the dotted lines, it is seen that in FIG. 10*a* that the exploring tip 130 has approached an abrupt curve in the wound track which is producing difficulty with the full insertion of the catheter into the track 100. The following descriptions illustrate this embodiment of my catheter system and my method for navigating such difficult wound tracks are used to fully navigate difficult wound tracks. In all there sections of this figure, the bulbous exploring tip 130 on the distal end of the stylet 142 is shown as being smaller than the outer diameter of the catheter, but experienced shows that it can be substantially larger, or smaller, with excellent results.

FIG. 10b shows the same setup as in FIG. 10a with the exception that now the exposed portion of the balloon 112 has now been inflated such that its enlargement has produced an enlargement of the wound track 100 proximal and distal to the inflated balloon segment. This wound track enlargement by balloon dilatation creates a wound track that is substantially easier to navigate with the extensible stylet's bulbous tip 130. The partially retracted sheath 150 permits the uncovered balloon to enlarge as shown but constrains the remainder portion of the balloon 112 form enlargement.

FIG. 10c shows the same setup as in FIG. 10b with the exception that now the stylet shaft 142 has been extended by the user pushing inward on the stylet handle (not shown). The extension of the tip 130 of the stylet 142 allows the preformed bend in the tip of the stylet to assume its preformed curve and the stylet can now be rotated using the stylet handle while it is being advanced and it now easily "finds" the wound track 100. The rotation of the stylet during its extension can be done manually by twisting and pushing simultaneously on the stylet handle, or it can be done using automatic rotation device 90 while the user alternately directs inward and outward pressure on the stylet in a maneuver which will easily find most wound tracks and allow the stylet to be advanced farther into the wound track as shown in this figure.

Once the stylet has been advanced further into the wound track, the catheter assembly is then advanced over the stylet into the wound track 100. During advancement of the catheter it is sometimes advantageous to leave the balloon inflated, and other time it is advantageous to deflate the balloon before advancing the catheter over the previously advanced stylet. This method of stylet wound track dilatation by distal balloon inflation, followed by stylet advancement further into the dilated wound track, and then followed by catheter advancement over the advanced stylet shaft can be repeated several times if need be until the entire wound track has been successfully navigated.

After the catheter has been fully inserted into the wound track, the sheath 150 is fully removed and the balloon is inflated to effect the desired tamponade of the bleeding within the wound track. The stylet may be left in the catheter with its tip 130 attached and the entire assembly removed once the patient reaches definitive care, such as when they are in the emergency department or the operating room. Alternatively, the stylet 142 may be removed by a firm pull on the stylet handle which will cause fracture of the attachment joint of the bulbous tip 130 with the stylet shaft 142. The exploring tip 130 is made of biocompatible and x-ray opaque material so that it can be left within the body indefinitely (as bullets often are) or easily retrieved when the patient is at surgery for definitive repair of their wounds.

Other Hemorrhage Control Uses of My Inventive Tourniquet Catheter System

One major purpose of my catheter system is to tamponade bleeding that would otherwise result in death quickly. This tamponadding of the bleeding will allow time for the trauma victim, military or civilian, to reach a site for definitive care such as the operating room.

However, an embodiment of my tamponade system, which may beneficially have a somewhat larger balloon constructed of a thinner and less puncture resistant balloon material, can also be effectively used in surgery to tamponade traumatic, surgical, or iatrogenic injuries. The catheter and its inflatable balloon can thus also be used as an adjustable pressure packing device, used singly or in multiples, to surround an organ, such as the liver or spleen, to control intraoperative bleeding from such organs or other bleeding prone vascular beds such as the presacral vascular plexus.

When used in this manner, the hemorrhage control devices, the balloon tamponade catheters, are placed within the patient in the OR and the proximal end of the catheter(s) is (are) brought out through the skin, preferably through an intentionally created "stab wound", so that the pressure within the tamponade catheter balloon(s) can be monitored and adjusted postoperatively. This ability to "pack an organ" with a balloon catheter, which is a non-porous device and which can be adjusted in its effective packing pressure from outside the body postoperatively, represents a major advancement over the current device and method for stanching such bleeding.

Currently, in the case of a major liver injury for example, the surgeon will use several, even many, large gauze pads ("lap pads") to create a firm packing around a bleeding liver in an attempt to control the bleeding by creating intra-abdominal pressure and by pressing the fractured liver pieces together as well as creating surface pressure to stanch bleeding from cut surfaces of the organ. Often times the patient is in very severe condition and near death and to preserve their life, after such packing, they will be closed up the abdomen without attempting definitive repair of the injuries. In this case, the patient is closed up with the liver packing left in place to provide postoperative hemostasis.

However, using this method of injured organ packing for hemorrhage control does not always work very well. Sometimes the packing is too loose and does not supply sufficient pressure for hemorrhage control. Conversely, sometimes the gauze packing is too tight and can consequently severely reducing blood flow in the both the injured and uninjured organs that can result in further damage to the patient. Either of these deviations from "optimal packing" will necessitate the return of the patient to the OR for adjustment of the packing. Such return to the OR is risky, painful, and expensive. However, even with optimal packing, the patient must eventually be returned to the OR to remove the packing in a few days, after the bleeding has stopped and the body is able to maintain hemostasis without the packing. The timing for this return for packing removal is tricky, since if done too soon, the patient will begin bleeding again. If done too late, the patient may develop a wound infection from the protracted presence of the large amount of porous foreign bodies in the abdomen or pelvis in the form of all the blood soaked gauze sponges used for packing in the first place. Such blood soaked sponges, held at body temperature, are a very good bacterial culture medium.

Conversely, when one or more of my inventive catheter system, with its large inflatable balloon of biocompatible material, is used in place of gauze sponges to pack the abdomen or pelvis to control hemorrhage, the pressure created by the balloon inflation can be measured externally and can be changed without taking the patient back to the OR as is required with gauze packing. Similarly, since the pressure in the balloons of my new devices can be reduced to zero at any time, it is possible to test the body's ability to maintain hemostasis without the pressure applied by my device's balloons. Thus the balloon's pressure can be reduced to zero, measured accurately externally. If the patient is able to maintain hemostasis without the packing pressure of the balloons for a day or two, it is probably safe to remove the catheters and their associated balloons. By using my devices for organ packing, it is not necessary to return the patient to the OR for removal as it is with sponge packing. This ability to non-surgically remove the catheters is because of their smooth surface and their very small volume when deflated, both characteristics being required to allow the entire catheter-balloon system to be removed without surgery simply by gentle, steady, traction on that portion of the catheter shaft which is external to the patient. Since the balloon is constructed of smooth surface material that is also biocompatible, such as for example 1-10 mil polyurethane, it does not stick to the internal organs and hence does not restart bleeding when removed as sometimes happens with the removal of gauze sponges which can stick to a bleeding organ and become embedded, and hence anchored, in the blood clots the body is creating to arrest the hemorrhage.

An additional advantage of my tamponade catheter system and method for wound packing at surgery is that since my device is not constructed of a porous material, it does not absorb blood and other tissue fluids and hence these fluids can be readily drained out of the body using standard wound drains, or by draining them from either the central lumen of my catheter or from additional drain lumens in another embodiment which includes them. The removal of these fluids gives an indication to care givers of the cessation, or the continuation, of internal bleeding and further prevents those fluids from being retained and hence the drained fluids do not become a culture medium for bacterial growth which can result in serious wound infections.

Other Aspects of My Invention not Covered in the Preceding Device and Methods Descriptions Whereas as the tamponade pressure created within tissues by my device is generally sufficient to stop arterial and venous bleeding, it does require that it be properly positioned fully within the wound track, and that the tissue of the wound track be of suitably firm consistency to allow the creation by the expansile element (the balloon) a pressure field in said tissue of sufficient magnitude to effect tamponade of all bleeding. The strength of the tissue pressure field must typically be at least slightly in excess of the blood pressure to be maximally effective, but lower pressures can at least slow bleeding.

Unfortunately, not all wounds are fully navigable for a variety of reasons, and not all wounds are in tissues that provide sufficient firmness to develop a pressure field capable of tamponadding vascular hemorrhage. To deal with these difficult wounds, it is a part of my catheter system to provide a vehicle or conduit for the introduction of hemostatic promoting materials (such as chitosan, fibrin, platelets, and other known clot enhancing substances) into the wound track to advantageously position them within the wound track at the site of bleeding for enhanced hemostasis. The delivery of one or more of these clot enhancers, using my catheter system as a vehicle for introduction, can be accomplished in a variety of ways, but the key factor in the effectivity of the clot enhancers when so introduced is that they are substantially deeper within the wound track than can be achieved by surface introduction as is currently done. The surface introduction of such agents is often ineffective if the bleeding wound tissue is substantially deeper than can be reached by pouring or pressurized injection of the liquid, gel, granules, or powder at the skin opening. Thus, by using my catheter with its various wound navigation design features and methods, the catheter can be placed substantially deeper than the skin wound as a point of subsequent deposition of any clot enhancing substance, even if it is impossible to advance it all the way to the wound track terminus or to its surface exit wound. The clot promoting substances can be coated on the catheter and the balloon and hence will come in contact with the wound track tissues when the catheter is navigated through the wound. Similarly, the substance can be injected through one or more specific lumens in the catheter tube which could be used for either drainage or alternatively the injection of a clot enhancing substance within the wound track itself.

These clot enhancer injection lumens could be the central lumen of the embodiment shown in FIG. 10 after removal of the stylet 142 or additional lumens in the catheter shaft with a terminal opening for substance injection into the wound from the catheter's tip. Optionally the device would contain a substance injection lumen with multiple side openings so that injection of the clotting agent would be immediately be dispersed within the wound track along the length of that injection lumen that had the multiple side openings and can be dispensed during the process of catheter introduction and navigation within the wound track.

Other embodiments of my invention provide other methods of clot enhancer introduction into the wound track. One such embodiment includes small holes in the balloon which will slowly release a clotting agent when said agent is a part of the balloon inflating medium. Such small holes will weep slowly and the fluid can be periodically replenished such that tamponadding pressure is maintained in the balloon if desired. Another design methodology to provide clot enhancing weeping from the balloon is to provide holes in the balloon which will open and weep the inner contents only if the pressure within the balloon is above a certain level. Thus, the pressure could be raised to cause weeping of clotting agent into the wound track and then the pressure could be lowered slightly to provide only tamponade pressure to the wound track. This embodiment provides clot enhancers and tamponade pressure without the inconvenience of having to periodically add inflation medium to the balloon to maintain tamponade pressure. Another method of maintaining balloon pressure is to connect the inflation lumen of the catheter to a bag of liquid, such as saline, which has the clotting agent dissolved in it and hence can be set at a height to maintain adequate tamponade pressure and also to provide clotting agent if that level is raised to create a balloon inflation pressure sufficient to open the weep holes in the balloon to allow passage of the clot enhancing liquid.

Granular or powder form clot enhancers can be forced into the wound track by pushing them through a large lumen with a stylet that is removable and reinsertable such that it becomes in effect like the ramrod used to load gunpowder into a muzzle loading rifle or pistol. In this embodiment, it is advantageous to have a large catheter central lumen to allow sufficient quantities of clot enhancing powders to be forced into the wound track to effect hemostasis.

A further aspect of my inventive catheter system that is unique and useful in proper tamponade of bleeding relates to determining the balloon required pressure to result in adequate tamponade. Since the nonelastic balloon, once inflated, is pressing firmly on the tissues, it is possible to determine the actual blood pressure within those adjacent tissues by utilizing the method of blood pressure measurement know as the oscillometric method. Use of this method of blood pressure determination by using my catheter within the wound track is accomplished as follows. The balloon is first inflated to a pressure believed to be slightly above the systolic pressure, as previously determined from the arm or leg using prior art devices. The pressure in the balloon is then slowly and continuously, or incrementally, deflated such that it passes through the regions of the systolic, then the mean, and then the systolic arterial pressure as the balloon pressure is slowly released. As is well know in the art, the amplitude of the small oscillations in pressure level measured in the balloon in response to each heart beat as the balloon pressure is reduced by deflation can be interpreted to give an accurate blood pressure reading. In the past these small oscillations are, in prior art devices, measured in the blood pressure cuff encircling the arm or leg, but in my invention, the oscillations measured are those in the tamponade balloon itself when it is inflated within the wound track. In this way, using oscillometric devices and methods well known in the art, the actual blood pressure in the tissues being compressed by the nonelastic balloon of my catheter can be easily measured and used as a guide for inflation to a level sufficient to adequately tamponade the bleeding. The use of this method is impossible with an elastic balloon tamponade balloon.

CONCLUSIONS, RAMIFICATIONS, AND SCOPE

The above descriptions of my internal compression catheter system and method of controlling hemorrhage from wounds, and its various embodiments encompassing different types of catheters, stylets, sheath, balloons, wound packing aspects and methods, clot enhancer introduction mechanisms and methods, contain may specifics as to design, features, and methods. These specific descriptions of devices and methods, and the various figures used to further illuminate certain aspects of my invention should not be construed as limiting the scope of the invention, but merely as providing descriptions, illustrations, and examples of some of the presently preferred embodiments, particularly embodiments that do not lend themselves to verbal description alone. Therefore, the foregoing is considered as illustrative only of the principles of the many and various aspects of the invention. Further, since numerous modifications, combinations, and changes will readily occur to those skilled in the art, it is desired to not limit the invention to the exact construction and operation shown or described; accordingly, all suitable modifications and equivalents may be resorted to, falling within the scope of the device invention and the method of hemorrhage control.

What is claimed is:

1. An emergency tamponade catheter for controlling bleeding from a penetrating or perforating wound in a patient prior to reach a site for definitive care such as the operating room and the like, the penetrating or perforating wound having a curved or irregular shaped wound track, comprising:
    a catheter extending from a proximal end and a distal end and having an inner catheter lumen;
    a bulbousor enlarged rounded exploring tip located on said distal end of said catheter for facilitating non-damaging insertion into the curved or irregular shaped wound of the patient;
    a non-elastic inflatable balloon secured to said catheter with said non-elastic inflatable balloon being in fluid communication with said inner catheter lumen of said catheter;
    a removable outer sheath overlaying said inflatable balloon for maintaining said inflatable balloon in a non-inflated condition to insert said inflatable balloon within the curved or irregular shaped wound of the patient;
    said removable outer sheath mating with said bulbousor enlarged rounded exploring tip to provide a smooth junction between said exploring tip and said removable outer sheath,
    a bendable flexible stiffening stylet receivable within said inner catheter lumen of said catheter;
    said bendable flexible stiffening stylet having a proximal end defining an external stylet handle;
    said bendable flexible stiffening stylet being pre-bent to aid in navigating said catheter into the curved or irregular shaped wound of the patient;
    said removable sheath maintaining said catheter in a straight condition against the prebend of said bendable flexible stiffening stylet for facilitating initial insertion into the curved or irregular shaped wound; a perforation in said removable outer sheath;
    a perforation in said removable outer sheath for partially retracting said removable outer sheath and enabling said pre-bend of said bendable flexible stiffening stylet to produce a curved configuration in proximity to said rounded exploring tip to assist in finding the true curved or irregular shaped wound track;
    said removable outer sheath and said stylet being removable for inflating said inflatable balloon by an introduction of a fluid through said inner catheter lumen of said catheter for enabling said inflated nonelastic inflatable balloon to create pressure within the wound of the patient to control bleeding from the curved or irregular shaped wound;
    said non-elastic inflatable balloon being deflatable for removing the emergency tamponade catheter from the curved or irregular shaped wound upon reaching a site for definitive care such as the operating room and the like;
    and a fitting coupled to said proximal end of said catheter for receiving a pump for inflating said non-elastic inflatable balloon.

2. An emergency tamponade catheter as in claim 1 wherein
    said inflatable balloon has an unconstrained volume of at least 65 ml;
    said nonelastic inflatable balloon requiring minimal pressure to be inflated to full unconstrained volume; and
    said nonelastic inflatable balloon being inflatable within the constraint of the wound by an introduction of a fluid through said internal catheter passageway of said catheter for permitting an accurate measurement of pressure applied to the wound of the patient by measuring the pressure within the balloon after inflation.

3. An emergency tamponade catheter as in claim 1 wherein said nonelastic inflatable balloon is made of a very thin, biocompatible material, to form a single walled balloon of the desired size and shape.

4. An emergency tamponade catheter as in claim 1 wherein said external stylet handle having at least one of a tactile means and a visual means of determining a rotational position of said stylet.

5. An emergency tamponade catheter as in claim 1 wherein said removable outer sheath is partially removable for inflating only a distal end of said inflatable balloon to dilate the wound of the patient for aiding in a deeper insertion of said catheter within the wound of the patient.

6. An emergency tamponade catheter as in claim 1 including an inner sheath for maintaining said non-elastic inflatable balloon in a rolled condition about said catheter and for protecting said non-elastic inflatable balloon upon removal of said removable outer sheath.

7. An emergency tamponade catheter as in claim 1 including a clot promoting substance coated on at least one of said catheter and said inflatable balloon for enhancing hemostatic action of the tamponade catheter.

8. An emergency tamponade catheter as in claim 1 including a second lumen defined in said catheter for introducing a clot promoting substance for enhancing hemostasis deep within the wound of the patient.

9. An emergency tamponade catheter as in claim 1 including a second lumen defined in said catheter for introducing a clot promoting substance in proximity to a distal end of said catheter; and
said catheter having multiple openings along said catheter communicating with said second lumen for dispersing said clot promoting substance along a length of said catheter.

10. An emergency tamponade catheter as in claim 1 including a clot promoting substance contained within said fluid introduced through said inner catheter lumen of said catheter; and
said inflatable member of said catheter having at least one hole for allowing leakage of said fluid containing said clot promoting substance into the wound track for assisting hemostasis.

11. An emergency tamponade catheter as in claim 1 including
a clot promoting substance contained within said fluid introduced through said inner catheter lumen of said catheter;
said inflatable member of said catheter having at least one hole for allowing leakage of said fluid containing said clot promoting substance into the wound track for assisting hemostasis; and
said hole releasing said clot promoting substance only upon a pressure in said inflatable balloon being greater than a specified amount.

12. An emergency tamponade catheter as in claim 1 including a drainage lumen defined in said catheter for draining body fluids from the wound of the patient.

13. An emergency device for controlling bleeding from a penetrating or perforating wound in a patient prior to reach a site for definitive care such as the operating room and the like, the penetrating or perforating wound having a curved or irregular shaped wound track, comprising:
a catheter extending from a proximal end and a distal end and having an inner catheter lumen;
a rounded exploring tip located on said distal end of said catheter for facilitating non-damaging insertion into the curved or irregular shaped wound of the patient;
said rounded exploring tip having a central hole communicating with said catheter lumen;
a non-elastic inflatable balloon secured to said catheter with said non-elastic inflatable balloon being in fluid communication with said inner catheter lumen of said catheter;
a removable sheath overlaying said inflatable balloon for maintaining said inflatable balloon in a non-inflated condition;
said removable sheath mating with said rounded exploring tip to provide a smooth junction between said exploring tip and said removable sheath;
a bendable flexible stiffening stylet having a distal end receivable within said inner catheter lumen of said catheter and extending into said central hole of said rounded exploring tip;
said bendable flexible stiffening stylet having a proximal end defining an external stylet handle;
said bendable flexible stiffening stylet being pre-bent prior to insertion into the curved or irregular shaped wound of the patient;
said removable sheath being stiff for maintaining said catheter in a straight condition against the pre-bend of said bendable flexible stiffening stylet for facilitating initial insertion into the wound;
a perforation in said removable outer sheath for partially retracting said removable outer sheath and enabling said pre-bend of said bendable flexible stiffening stylet to bend said catheter to produce a curved configuration in proximity to said rounded exploring tip to assist in finding the true curved or irregular shaped wound track;
said removable outer sheath and said stylet being removable for inflating said inflatable balloon by an introduction of a fluid through said inner catheter lumen of said catheter for enabling said inflated nonelastic inflatable balloon to create pressure within the curved or irregular shaped wound of the patient to control bleeding therefrom from the curved or irregular shaped wound;
said non-elastic inflatable balloon being deflatable for removing the emergency tamponade catheter from the curved or irregular shaped wound upon reaching a site for definitive care such as the operating room and the like;
and a fitting coupled to said proximal end of said catheter and configured for receiving a pump for inflating said non-elastic inflatable balloon.

14. An emergency tamponade catheter for controlling bleeding from a penetrating or perforating wound in a patient prior to reach a site for definitive care such as the operating room and the like, the penetrating or perforating wound having a curved or irregular shaped wound track, comprising:
a catheter extending from a proximal end and a distal end and having an inner catheter lumen;
a bulbous or enlarged rounded exploring tip located on said distal end of said catheter for facilitating non-damaging insertion into the curved or irregular shaped wound of the patient;
a non-elastic inflatable balloon secured to said catheter with said non-elastic inflatable balloon being in fluid communication with said inner catheter lumen of said catheter;
a removable outer sheath overlaying said inflatable balloon for maintaining said inflatable balloon in a non-inflated condition to insert said inflatable balloon within the curved or irregular shaped wound of the patient;
said removable outer sheath mating with said bulbous or enlarged rounded exploring tip to provide a smooth junction between said exploring tip and said removable outer sheath,
a bendable flexible stiffening stylet receivable within said inner catheter lumen of said catheter;
said bendable flexible stiffening stylet having a proximal end defining an external stylet handle;
a perforation in said removable outer sheath for partiallyretracting said removable outer sheath and enabling said non-elastic inflatable balloon to be partially inflated in proximity to said distal end of said bendable flexible stiffening stylet for forming a pilot balloon to expand the curved or irregular shaped wound track to further insertion into the wound track;
said removable outer sheath being removed for further inflating said inflatable balloon by an introduction of a fluid through said inner catheter lumen of said catheter for enabling said inflated non-elastic inflatable balloon to create pressure within the curved or irregular shaped wound of the patient to control bleeding therefrom from the curved or irregular shaped wound; and said non-elastic inflatable balloon being deflatable for removing the emergency tamponade catheter from the curved or irregular shaped wound upon reaching a site for definitive care such as the operating room and the like.

15. An emergency tamponade catheter for controlling bleeding from a penetrating or perforating wound in a patient, the penetrating or perforating wound having a curved or irregular shaped wound track, comprising:

a catheter extending from a proximal end and a distal end and having an inner catheter lumen;

a bulbousor enlarged rounded exploring tip located on said distal end of said catheter for facilitating non-damaging insertion into the curved or irregular shaped wound of the patient;

a non-elastic inflatable balloon secured to said catheter with said non-elastic inflatable balloon being in fluid communication with said inner catheter lumen of said catheter;

a removable outer sheath overlaying said inflatable balloon for maintaining said inflatable balloon in a non-inflated condition to insert said inflatable balloon within the curved or irregular shaped wound of the patient;

said removable outer sheath mating with said bulbousor enlarged rounded exploring tip to provide a smooth junction between said exploring tip and said removable outer sheath, a stiffening stylet receivable within said inner catheter lumen of said catheter, said stiffening stylet having a proximal end defining an external stylet handle;

said stiffening stylet aiding in navigating said catheter into the curved or irregular shaped wound of the patient;

a perforation in said removable outer sheath for removing said removable outer sheath and said stylet being removable for inflating said inflatable balloon by an introduction of a fluid through said inner catheter lumen of said catheter for enabling said inflated non-elastic inflatable balloon to create pressure within the wound of the patient to control bleeding from the curved or irregular shaped wound; and a fitting coupled to said proximal end of said catheter and configured for receiving a pump for inflating said non-elastic inflatable balloon.

16. The emergency tamponade catheter as set forth in claim 15, wherein said pump includes an integral pressure gauge for measuring the pressure within said non-elastic inflatable balloon.

17. The emergency tamponade catheter as set forth in claim 15, further including a check valve coupled to said catheter to aid in the inflation and pressure maintenance of said non-elastic inflatable balloon and permit removal of said hand bulb pump before transporting the patient a definitive care site such as the operating room or the like.

18. An emergency tamponade catheter for controlling bleeding from a penetrating or perforating wound in a patient, the penetrating or perforating wound having a curved or irregular shaped wound track, comprising:

a catheter extending from a proximal end and a distal end and having an inner catheter lumen;

a bulbousor enlarged rounded exploring tip located on said distal end of said catheter for facilitating non-damaging insertion into the curved or irregular shaped wound of the patient;

a non-elastic inflatable balloon secured to said catheter with said non-elastic inflatable balloon being in fluid communication with said inner catheter lumen of said catheter;

a removable outer sheath overlaying said inflatable balloon for maintaining said inflatable balloon in a non-inflated condition to insert said inflatable balloon within the curved or irregular shaped wound of the patient;

said removable outer sheath mating with said bulbousor enlarged rounded exploring tip to provide a smooth junction between said exploring tip and said removable outer sheath;

a bendable flexible stiffening stylet receivable within said inner catheter lumen of said catheter to aid in navigating said catheter in the curved or irregular shaped wound of the patient;

a perforation in said removable outer sheath for partially retracting said removable outer sheath and inflating said inflatable balloon by an introduction of a fluid through said inner catheter lumen of said catheter for enabling said inflated non-elastic inflatable balloon to create pressure within the wound of the patient to control bleeding from the curved or irregular shaped wound.

\* \* \* \* \*